United States Patent
Fajdetic et al.

(10) Patent No.: US 7,358,367 B2
(45) Date of Patent: Apr. 15, 2008

(54) PRESENT INVENTION RELATES TO THE NEW 3-DECLADINOSYL DERIVATIVES OF 9-DEOXO-9A-AZA9A-HOMOERYTHROMYCIN A 9A, 11-CYCLIC CARBAMATES

(75) Inventors: Andrea Fajdetic, Zagreb (HR); Gabrijela Kobrehel, Zagreb (HR); Gorjana Lazarevski, Zagreb (HR); Stjepan Mutak, Zagreb (HR)

(73) Assignee: GlaxoSmithKline istrazivacki Centar Zagreb d.o., Zagreb (HR)

( * ) Notice: Subject to any disclaimer, the term of this patent is extended or adjusted under 35 U.S.C. 154(b) by 210 days.

(21) Appl. No.: 10/527,940

(22) PCT Filed: Sep. 26, 2003

(86) PCT No.: PCT/HR03/00051

§ 371 (c)(1),
(2), (4) Date: Sep. 29, 2005

(87) PCT Pub. No.: WO2004/029067

PCT Pub. Date: Apr. 8, 2004

(65) Prior Publication Data

US 2006/0154878 A1    Jul. 13, 2006

(30) Foreign Application Priority Data

Sep. 27, 2002 (HR) ............................ P 20020779 A

(51) Int. Cl.
C07D 498/08 (2006.01)
(52) U.S. Cl. .................................................... 548/218
(58) Field of Classification Search ................ 549/267; 548/218
See application file for complete search history.

(56) References Cited

U.S. PATENT DOCUMENTS

| 4,328,334 A | | 5/1982 | Kobrehel et al. |
| 5,434,140 A | * | 7/1995 | Kobrehel et al. ............. 514/30 |
| 5,527,780 A | | 6/1996 | Agouridas et al. |
| 5,543,400 A | | 8/1996 | Agouridas et al. |
| 5,614,614 A | | 3/1997 | Agouridas et al. |

FOREIGN PATENT DOCUMENTS

| EP | 0606062 | 7/1994 |
| WO | 9920639 A2 | 4/1999 |
| WO | 99/51616 A1 | 10/1999 |
| WO | 0063223 A1 | 10/2000 |

OTHER PUBLICATIONS

Lazarevski et al., "A Comparative NMR and Moleculare-Modeling Study Among Some Macrolides and Azalides With Different Antibacterial Properties." Infections Disease and Therapy, Dekker (ed.), New York, NY, vol. 18, 1995, pp. 203-211.

(Continued)

*Primary Examiner*—Taofiq Solola
(74) *Attorney, Agent, or Firm*—Karen L. Prus

(57) ABSTRACT

The present invention relates to the new 3-decladinosyl derivatives of 9-de-oxo-9a-aza9a-homoerythromycin A 9a,11-cyclic carbamate of the general formula (I), their pharmaceutically acceptable addition salts with inorganic or organic acids and their hydrates, wherein $R_1$ individually stands for hydrogen, hydroxyl or a group of the formula (II), wherein X individually stands for $C_1$-$C_6$alkyl group, $C_2$-$C_6$alkenyl group or X individually stands for $C_1$-$C_6$alkyl group with at least one incorporated O, S or N atom or X individually stands for $(CH_2)_n$—Ar or X individually stands for $(CH_2)_n$-heterocycloalkyl, wherein $(CH_2)_n$ individually stands for alkyl, wherein n is 1-10, with or without incorporated atom O, S or N, wherein Ar individually stands for 5-10-membered monocyclic or bycyclic aromatic ring with 0-3 atom O, S or N, unsubstituted or substituted with 1-3 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl stands for unaromatic, partially or completely saturated 3-10-membered monocyclic or bicyclic ring system, which includes 3-8-membered monocyclic or bicyclic ring, which includes 6-membered aromatic or heteroaromatic ring connected with a unaromatic ring with or without incorporated O, S or N atom, unsubstituted or substituted with 1-4 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1C_3$alkil, —C(O)—, COOH or $R_1$ together with $R_2$ stands for ketone, $R_2$ individually stands for hydrogen or together with $R_1$ stands for ketone or together with $R_3$ stands for ether, $R_3$ individually stands for hydroxyl, a group of the formula —OX or together with $R_2$ stands for ether, $R_4$ individually stands for hydrogen, $C_1$-$C_4$alkyl group or $C_2$-$C_4$alkenyl group, and $R_5$ individually stands for hydrogen or hydroxyl protected group, to intermediates for synthesis of other macrolide compounds with antibacterial activity, to the process for their preparation, to their pharmaceutically acceptable addition salts with inorganic or organic acids and their hydrates, to the process for the preparation of pharmaceutical compositions, as well as the use of pharmaceutical compositions for treating bacterial infections

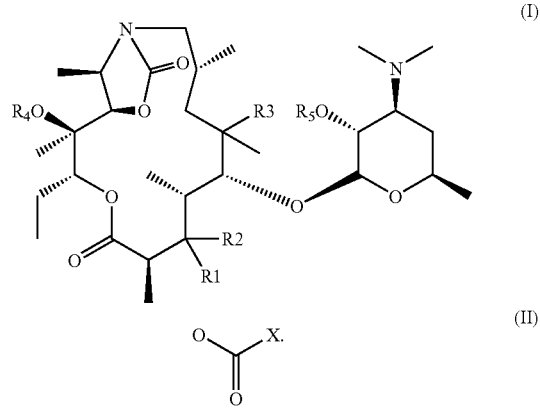

15 Claims, No Drawings

OTHER PUBLICATIONS

Kobrehel et al., "9a, 11-cyclic carbamates of 15-membered azalides." The Journal of Antibiotics, vol. 46, 1993, pp. 1239-1245.

McGuire et al., "Ilotycin," A New Antibiotic, Antibiot. Chemother., 1952, 2(1):281/283.

Krist at al., New Directions for Macrolide Antibiotics: Pharmacokinetics and Clinical Efficacy, Antimicrob. Agents and Chemother., 1989, 33(9):1419-1422.

Jamjian et al., In Vitro Evaluation of a Novel Ketolide Antimicrobial Agent, RU-64004, Antimicrob. Agents Chemother., 1997, 41(2):454-459.

Anderson, Steven L., et al.; Prophylaxis of *Plasmodium falciparum* Malaria with Azithromycin Administered to Volunteers; Annals of Internal Medicine; Nov. 15, 1995; 123, 10; 771-773.

Puri, S. K, Dutta, G.P.; Spectrum of the Antimalarial Activity of a New Macrolide Antibiotic Midecamycin in Mice and Monkeys; Chemotherapy; 1989; 35; 187-192.

Taylor, Walter R. J., et al.; Malaria Prophylaxis using Azithromycin: A Double-Blind, Placebo-Controlled Trial in Irian Jaya, Indonesia; Clinical Infectious Diseases; Jan. 1999; 28, 1; 74-81.

Luger, P. and Maier, R.; Molecular structure of 9-deoxy-11-deoxy-9-11-(imino(2-(2-methoxyethoxy)ethylidene)oxy)-(9S)-erythromycin, a new erythromycin derivative; Journal of Crystal and Molecular Structure; 1979; 9, 6; 328-338; 1.

Egan, Richard S., et al.; Configuration of 9-Imino Derivatives of Erythromycin; J. Org. Chem.; 39, 17; 1974; 2492-2494.

Djokic, S. and Tamburasev, Z.; Erythromycin Study: 9-Amino-3-0-Cladinosyl-5-0-Despsaminyl-6,11,12-Tryhydroxy-2,4,6,8,10,12-Hexamethylpentadecane-13-Olide; Tetrahedron Letters; 1967; 17; 1645-1647.

Kurath, P., et al.; Acid Degradation of Erythomycin A and Erythromycin B; Experentia; 1970; 27, 4; 362.

* cited by examiner

PRESENT INVENTION RELATES TO THE NEW 3-DECLADINOSYL DERIVATIVES OF 9-DEOXO-9A-AZA9A-HOMOERYTHROMYCIN A 9A, 11-CYCLIC CARBAMATES

This application is a National Stage under 35 U.S.C. §371 of PCT International Application No. PCT/HR03/00051, filed Sep. 26, 2003, which claims the benefit under 35 U.S.C. §119(e) of prior Croatian Application No. P20020779A, filed Sep. 27, 2002. The International Application was published in English on Apr. 8, 2004 as WO 2004/029067 A1 under PCT Article 21(2).

1) TECHNICAL FIELD OF THE INVENTION

A 61 K 31/70, C0 7H 17/08

2) TECHNICAL PROBLEM

The invention relates to novel compounds from the class of macrolide antibiotics. Particularly, the invention relates to novel 3-decladinosyl derivatives from the class of 9-deoxo-9-dihydro-9a-aza-9a-homoerythromycin A 9a,11-cyclic carbamates, to their pharmaceutically acceptable addition salts with inorganic or organic acids, to their hydrates, to the process for their preparation, to the process for preparation of their pharmaceutical compositions and to the use thereof as antibiotics or intermediates for the synthesis of other macrolide antibiotics.

3) PRIOR ART

Macrolides are well known agens for treating broad spectrum of infections. Erythromycin A (McGuire; Antibiot. Chemother., 1952; 2: 281) has been for more than 40 years considered as safe and efficient agent for the treatment of respiratory and genital infections caused by Gram-positive and by some Gram-negative bacteria, some species of *Legionella, Mycoplasna, Clilamidia* and *Helicobacter*. By oxidation of C-9 ketone of erythromycin and subsequent Beckmann rearrangement and reduction, 9-deoxo-9a-aza-9a-homoerythromycin A, the first 15-membered macrolide antibiotics with 9a-amino group incorporated in aglycone ring, is obtained (Kobrehel G. et al., U.S. Pat. No. 4,328,334 May 1982).

By O-methylation of C-6 hydroxyl group of erythromycin clarithromycin is obtained (6-O-metil-erythromycin A) (Morimoto S. et al., J. Antibiotics, 1984, 37, 187). In comparison with erythromycin A, clarithromycin is more stable and shows enhanced in vitro activity against Gram-positive strains (Kirst H. A. et al., Antimicrob. Agents and Chemother., 1989, 1419).

In a similar manner by reaction of 9-deoxo-9-dihydro-9a-aza-9a-homoerythromycin A with benzyloxycarbonyl chloride via 2'-O,(3',9a-di-N)-tris(benzyloxycarbonyl)-derivative correspondent 9a,11-cyclic carbamate and their 12-O-methyl- and 12,4"-di-O-methyl-derivatives (Kobrehel G. et al., J. Antibiotics, 1993, 46, 1239) were synthesized.

It is known as well that recent research on 14-membered macrolides has lead to the discovery of a new type of macrolide antibiotics, namely ketolides. Instead of the neutral sugar L-cladinose known for its instability even in a weakly acidic medium, these compounds possess a keto group on C-3 position (Agouridas C. et al., EP 596802 A1 May 1994, Le Martret O., FR 2697524 A1 May 1994). Ketolides show a significantly better activity against MLS (macrolide, lincosamide and streptogramin B) induced-resistant organisms (Jamjian C., Antimicrob. Agents Chemother., 1997, 41, 485).

Object of the present invention are 3-decladinosyl derivatives of 9-deoxo-9a-aza-9a-homoerythromycin A 9a,11-cyclic carbamate, their pharmaceutically acceptable addition salts with inorganic or organic acids, their hydrates, methods and intermediates for their preparation as well as preparation and application methods of pharmaceutical preparations.

4) DESCRIPTION OF TECHNICAL PROBLEM WITH EXAMPLES

The invention relates to:
i) novel 3-decladinosyl derivatives of 9-deoxo-9a-aza-9a-homoerythromycin A 9a,11-cyclic carbamate, their pharmaceutically acceptable addition salts with inorganic or organic acids and their hydrates,
ii) methods for preparation of novel 3-decladinosyl derivatives of 9-deoxo-9a-aza-9a-homoerythromycin A 9a,11-cyclic carbamate, their pharmaceutically acceptable addition salts with inorganic or organic acids and their hydrates,
iii) use of novel 3-decladinosyl derivatives of 9-deoxo-9a-aza-9a-homoerythromycin A 9a,11-cyclic carbamate, their pharmaceutically acceptable addition salts with inorganic or organic acids and their hydrates as antibiotics or
iv) use of novel 3-decladinosyl derivatives of 9-deoxo-9a-aza-9a-homoerythromycin A 9a,11-cyclic carbamate, their pharmaceutically acceptable addition salts with inorganic or organic acids and their hydrates as intermediates for the synthesis of other macrolide antibiotics.

Novel 3-decladinosyl derivatives of 9-deoxo-9a-aza-9a-homoerythromycin A 9a,11-cyclic carbamate of the general formula (I),

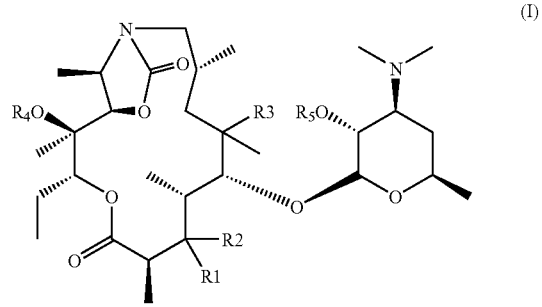

their pharmaceutically acceptable addition salts with inorganic or organic acids and their hydrates, wherein $R_1$ individually stands for hydrogen, hydroxyl or a group of the formula (II),

(II)

wherein

X individually stands for $C_1$-$C_6$alkyl group, $C_2$-$C_6$alkenyl group or X individually stands for $C_1$-$C_6$alkyl group with at least one incorporated O, S or N atom or X individually stands for $(CH_2)_n$—Ar or X individually stands for $(CH_2)_n$-heterocycloalkyl, wherein $(CH_2)_n$ individually stands for alkyl, wherein n is 1-10, with or without incorporated atom O, S or N, wherein Ar individually stands for 5-10-membered monocyclic or bicyclic aromatic ring with 0-3 atom O, S or N, unsubstituted or substituted with 1-3 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl stands for unaromatic, partially or completely saturated 3-10-membered monocyclic or bicyclic ring system, which includes 3-8-membered monocyclic or bicyclic ring, which includes 6-membered aromatic or heteroaromatic ring connected with a unaromatic ring with or without incorporated O, S or N atom, unsubstituted or substituted with 1-4 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkil, —C(O)—, COOH or $R_1$ together with $R_2$ stands for ketone, $R_2$ individually stands for hydrogen or together with $R_1$ stands for ketone or together with $R_3$ stands for ether, $R_3$ individually stands for hydroxyl, a group of the formula —OX or together with $R_2$ stands for ether, $R_4$ individually stands for hydrogen, $C_1$-$C_4$alkyl group or $C_2$-$C_4$alkenyl group, and $R_5$ individually stands for hydrogen or hydroxyl protected group are subject of this invention.

Term <<hydroxyl protected group>> includes, but is not limited on benzoyl, benzyloxycarbonyl, acetyl or substituted silyl group in order to block the undesired reaction due the synthesis (T. H. Green and P. G. M. Wuts, Protective Groups in Organic Synthesis, 3rd edition, John Wiley & Sons, New York, 1999).

Compounds given by general formula (I), wherein $R_1$, $R_2$, $R_3$, $R_4$, $R_5$ and X have the meaning as defined above could be prepared by methods described in this invention. Methods of preparations, which also are subject of this invention, are illustrated by schemes 1. and 2.:

Scheme 1.

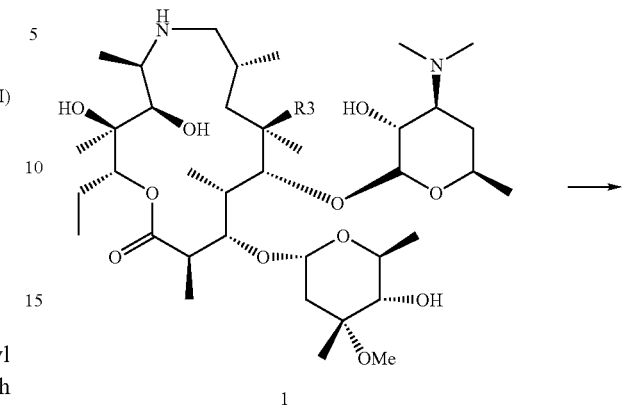

1

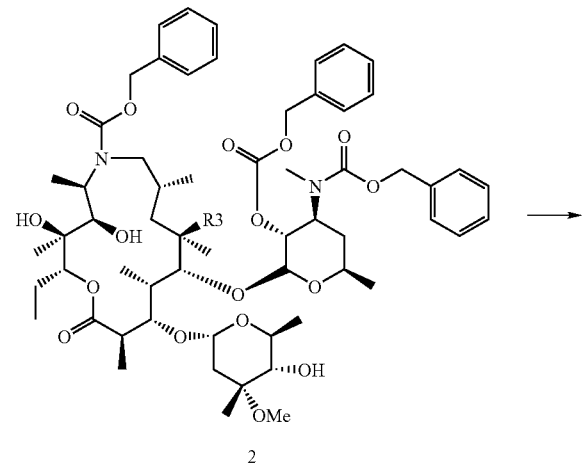

2

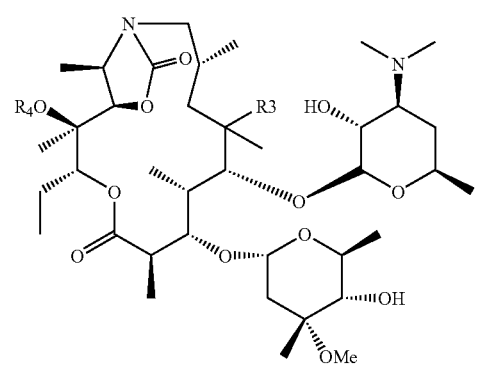

3

Scheme 2.

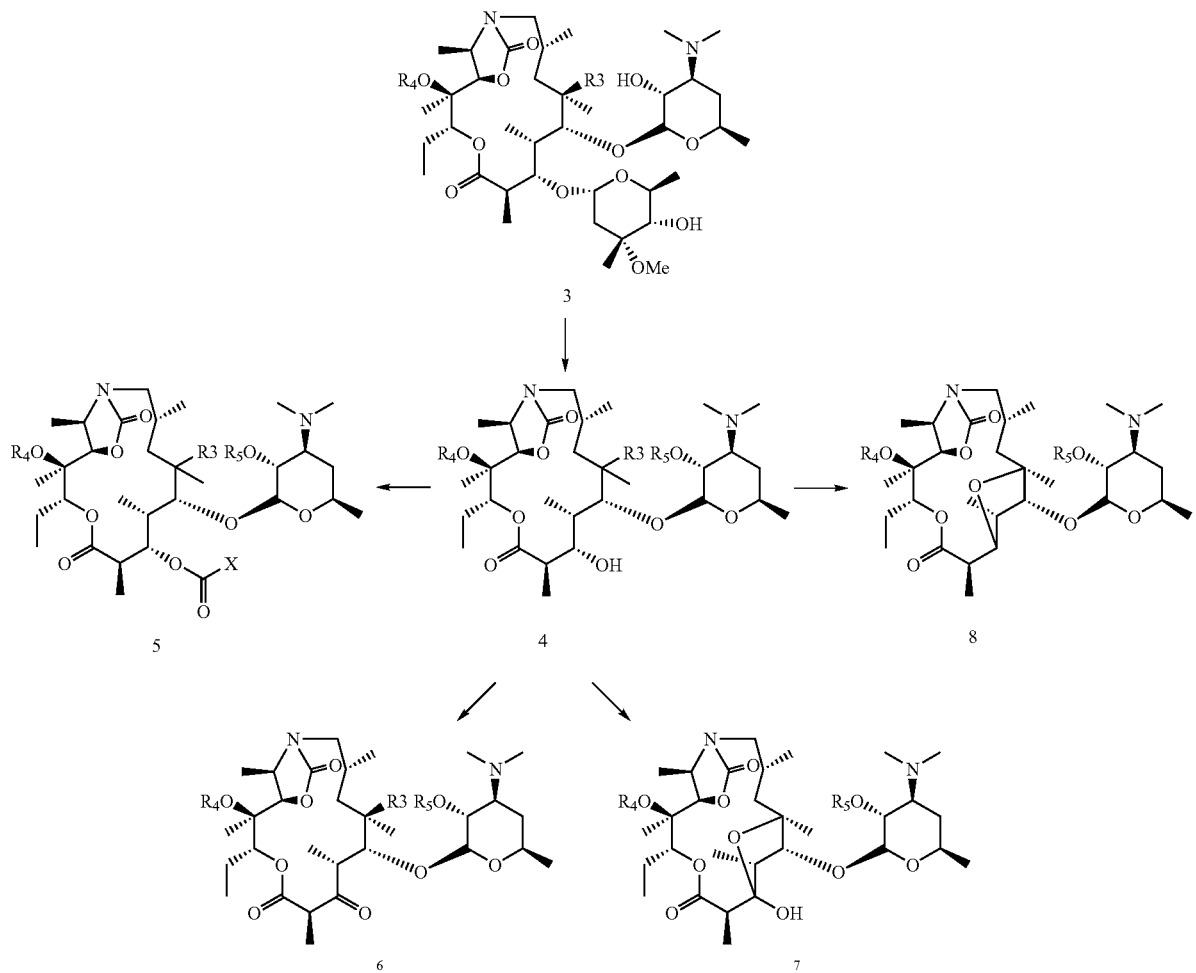

Starting compound described in scheme 1. for synthesis of compounds, which are subject of this invention are prepared by methods described in patent Kobrehel G. et al., U.S. Pat. No. 4,328,334 May 1982 and in the article A. Denis and C. Agouridas, Bioorg. Med. Chem. Lett. 1998, 8, 2427 (compound of general formula 1), and in the article Kobrehel G. et al., J. Antibiotics 1993, 46, 1239. (compounds 2 and 3).

Step 1.

The first step of the invention includes a preparation of compounds given by general formula 4 (scheme 2.), wherein $R_3$ individually stands for hydroxyl or for group of the formula —OX, $R_5$ stands for hydrogen, wherein $R_4$ and X have the above meanings, by hydrolysis of the compound of the general formula 3 (scheme 2.), wherein $R_3$ individually stands for hydroxyl or the group of the formula —OX, wherein $R_4$ and X have the above meanings with strong acids, preferably with 0.25-1.5 N hydrochloric acid, in a mixture of water and lower alcohols, preferably methanol, ethanol or isopropanol, over 10-30 hours at room temperature.

Step 2.

3-Decladinosyl derivatives obtained in Step 1. are subjected to a selective acylation of the hydroxyl group on 2'-position. Acylation is carried out with chlorides or anhydrides of carboxylic acids with up to 4 carbon atoms, preferably with acetic acid anhydrides, in the presence of inorganic or organic base, in a reaction-inert solvent at a temperature from 0-30° C., yielding 2'-O-acyl derivatives of the formula 4 (scheme 2.), wherein $R_5$ stands for hydroxyl protected group, preferably acetyl, $R_3$ individually stands for hydroxyl or group of the formula —OX, wherein $R_4$ and X have the above meanings.

As suitable bases sodium hydrogencarbonate, sodium carbonate, potassium carbonate, triethylamine, pyridine, tributylamine are used. As a suitable inert solvent methylene chloride, dichlorethane, acetone, pyridine, ethyl acetate, tetrahydrofuran are used.

2'-O-Acetyl derivatives from the Step 2. are optionally subjected to a reaction with mixed anhydrides of carboxylic acids of the formula Y—COO—R', wherein Y individually stands for hydrogen or for group X, which is defined above, wherein R' stands for the group which is usually used for preparation of mixed anhydrides as pivaloyl-, p-toluensulphonyl-, isobutoxycarbonyl-, etoxycarbonyl- or isopropoxycarbonyl-group, in the presence of inorganic or organic base, in a reaction-inert solvent, preferably methylene chloride at a temperature from 0-30° C. for 3-100 hours yielding compounds of the formula 5 (scheme 2.), wherein $R_3$ individually stands for hydroxyl or the group of the formula —OX, wherein $R_5$ stands for acyl and substituents $R_4$ and X have the above meanings. Formed compounds are subsequently subjected to deprotection with lower alcohols, preferably in methanol, at a temperature from room temperature to the reflux temperature of the solvent, yielding a compound of the formula 5, wherein $R_5$ stands for hydrogen, wherein $R_3$, $R_4$ and X have the above meanings, or optionally 2'-O-acetyl derivatives from the Step 2., wherein $R_3$ stands for the group of the formula —OX and all other substituents have the meanings as in the Step 2. are subjected to oxidation of the hydroxyl group in the C-3 position of an aglycone ring according to a modified Moffat-Pfitzner process with N,N-dimethylaminopropyl-3-ethyl-carbodiimide in the presence of dimethylsulfoxide and pyridinium trifluoracetate as a catalyst in a inert organic solvent, preferably in methylene chloride, at a temperature from 10° C. to room temperature, yielding compounds of the formula 6 (scheme 2.), wherein $R_3$ stands for the group of the formula OX, $R_5$ stands for acetyl and supstituents $R_4$ and X have the above meanings. Formed compounds are subsequently subjected to deprotection with lower alcohols, preferably in methanol, at a temperature from room temperature to the reflux temperature of the solvent, yielding a compound of the formula 6, wherein $R_3$ stands for hydrogen and all other supstituents have the above meanings. Alternatively it is possible to oxidize C-3 hydroxyl group using Dess Martin periodinane reagens or optionally 2'-O-acetyl derivatives from the Step 2., wherein $R_3$ stands for hydroxyl and all other supstituents have the meanings as in the Step 2. are subjected to oxidation described to obtain compounds of the formula 6, where compounds with 3,6-hemiketal structure given by formula 7, wherein $R_5$ stands for acyl and $R_4$ has the above meanings are formed. Formed compounds are subsequently subjected to deprotection with lower alcohols, preferably in methanol, at a temperature from room temperature to the reflux temperature of the solvent, yielding a compound of the formula 7, wherein $R_5$ stands for hydrogen and $R_4$ has the above meanings or optionally 2'-O-acetyl derivatives from the Step 2., wherein $R_3$ stands for hydroxyl and all other supstituents have the meanings as in the Step 2. are subjected to adequate reagents for dehydratation, preferably methylsulfonyl anhydride to transform hydroxyl group at position 3 in good leaving group, in an inert organic solvent, preferably in pyridine, at a temperature from room temperature to the reflux temperature of the solvent for 10-50 hours. Formed intermediate is subsequently subjected to reaction of elimination with adequate reagents, preferably sodium hydride, in a inert organic solvent, preferably in tetrahydrofuran, at a temperature from 10° C. to room temperature, yielding 3,6-cyclic ether of the formula 8, wherein $R_5$ stands for acetyl and $R_4$ has the above meanings. Formed compounds are subsequently subjected to deprotection with lower alcohols, preferably in methanol, at a temperature from room temperature to the reflux temperature of the solvent, yielding a compound of the formula 8, wherein $R_5$ stands for hydrogen and $R_4$ has the above meanings.

Pharmaceutically acceptable addition salts which are also subject of this invention are prepared by reaction of new compounds of the general formula (I) with at least one eqimolar amounts of suitable inorganic or organic acid as chloride, iodide, sulphate, phosphate, acetic, propionic, trifluoracetic, maleinic, citric, stearic, jantaric, ethyljantaric, mathansulphonic, p-toluensulphonic, laurylsulphonic and other acids in reaction inert solvent. Addition salts are isolated by filtration (if they are insoluble in used solvent), by precipitation, by evaporating the solvent or by liophilisation.

The process is illustrated by the following examples, which do not limit the scope of the invention in any way.

Example 1

3-Decladinosyl-3-oxy-9-deoxo-9-dihydro-9a-aza-9a-homoerythromycin A 9a,11-cyclic carbamate To a solution of 9-deoxo-9-dihydro-9a-aza-9a-homoerythromycin A 9a,11-cyclic carbamate (5.18 g) in 96% ethanol (150 ml) 0.25N hydrochloric acid (50 ml) was added and the reaction mixture was stirred for 48 hours at room temperature. Ethanol was evaporated, $CHCl_3$ (150 ml) was added and the pH of the mixture was about pH 1.2. Layers were separated and the water layer extracted two more times with $CHCl_3$. PH value of water layer was adjusted on pH 9.5 and then extracted three times with $CHCl_3$. Combined organic extracts at pH 9.5 were rinsed with brine, dried over $K_2CO_3$ and evaporated yielding 3.96 g of the title product. This product could be optionally purified by lowpressure chromatography on a silica gel column using the system $CH_2Cl_2$:MeOH:$NH_4OH$=90:9:0.5. The combining and evaporating of chromatographically homogenous fractions gave the title product with following physical-chemical constants:

TLC $CH_2Cl_2$:MeOH:$NH_4OH$=90:9:0.5 0.382

IR (KBr) cm$^{-1}$ 3442, 2973, 2937, 2879, 2789, 1743, 1638, 1459, 1417, 1380, 1166, 1113, 1078, 1049, 1001, 947, 915, 897, 770, 670.

ESI-MS, MH$^+$ 603.6

$^1$H NMR (300 MHz, CDCl$_3$) δ 5.14 (H-13), 4.45 (H-1'), 4.26 (H-11), 3.78 (H-3), 3.60 (H-5'), 3.56 (H-5), 3.53 (H-9a), 3.49 (H-10), 3.26 (H-2'), 2.58 (H-2), 2.51 (H-3'), 2.35 (H-8), 2.34 (H-9b), 2.26/3'N(CH$_3$)$_2$/, 2.15 (H-4), 1.91 (H-14a), 1.68 (H-4'a), 1.52 (H-14b), 1.50 (H-7a), 1.33 (6-CH$_3$), 1.31 (10-CH$_3$), 1.30 (2-CH$_3$), 1.26 (5'-CH$_3$), 1.25 (H-4'b), 1.22 (12-CH$_3$), 1.16 (H-7b), 1.01 (4-CH$_3$), 1.01 (8-CH$_3$), 0.88 (14-CH$_3$).

$^{13}$C NMR (75 MHz, CDCl$_3$) δ 174.9 (C-1), 156.4 (9a,11 C=O), 106.0 (C-1'), 93.6 (C-5), 78.2 (C-11), 77.8 (C-3), 75.6 (C-13), 73.7 (C-12), 71.5 (C-6), 70.9 (C-9), 70.2 (C-2'), 69.7 (C-5'), 65.1 (C-3'), 58.4 (C-10), 49.5 (C-9), 44.3 (C-2), 39.9/3'N(CH$_3$)$_2$/, 36.6 (C-7), 36.5 (C-4), 27.9 (C-4'), 25.4 (6-CH$_3$), 25.3 (C-8), 20.9 (5'-CH$_3$), 20.2 (8-CH$_3$), 20.2 (C-14), 15.7 (2-CH$_3$), 15.0 (12-CH$_3$), 13.8 (10-CH$_3$), 10.1 (14-CH$_3$), 7.5 (4-CH$_3$).

Example 2

2'-O-Acetyl-3-decladinosyl-3-oxy-9-deoxo-9-dihydro-9a-aza-9a-homoerythromycin A 9a,11-cyclic carbamate To a solution of 3-decladinosyl-3-oxy-9-deoxo-9-dihydro-9a-aza-9a-homoerythromycin A 9a,11-cyclic carbamate (3.0 g, 4.98 mmola) from Example 1. in $CH_2Cl_2$ (100 ml), $NaHCO_3$ (1.09 g, 13.0 mmola) and acetic acid anhydride (0.62 ml, 6.57 mmola) were added and it was then stirred for 4 hours at room temperature. Onto the reaction mixture a saturated $NaHCO_3$ solution was added, the layers were separated and the aqueous one was extracted two more times with $CH_2Cl_2$. The combined organic extracts were rinsed with saturated $NaHCO_3$ solution and water and evaporated yielding the title product (2.93 g) with following physical-chemical constants:

TLC CH$_2$Cl$_2$:MeOH:NH$_4$OH=90:9:0.5 0.418
IR (KBr) cm$^{-1}$ 3485, 2973, 2879, 2786, 1747, 1579, 1461, 1417, 1377, 1249, 1168, 1113, 1049, 1006, 947, 899, 810, 770.
FAB-MS, MH$^+$ 645.7

Example 3

3-Decladinosyl-3-oxy-12-O-methyl-9-deoxo-9-dihydro-9a-aza-9a-homoerythromycin A 9a,11-cyclic carbamate Method A:

To a solution of 12-O-methyl-9-deoxo-9-dihydro-9a-aza-9a-homoerythromycin A 9a,11-cyclic carbamate (1.8 g) in 96% ethanol (50 ml) 0.25N hydrochloric acid (15 ml) was added and the reaction mixture was stirred for 48 hours at room temperature. Ethanol was evaporated, CHCl$_3$ (50 ml) was added and the pH of the mixture was about pH 0.75. Layers were separated and the water layer extracted two more times with CHCl$_3$. PH value of water layer was adjusted on pH 9.5 and then extracted three times with CHCl$_3$. Combined organic extracts at pH 9.5 were rinsed with brine, dried over K$_2$CO$_3$ and evaporated yielding 0.69 g of the title product. This product could be optionally purified by lowpressure chromatography on a silica gel column using the system CH$_2$Cl$_2$:MeOH:NH$_4$OH=90:9:0.5. The combining and evaporating of chromatographically homogenous fractions gave the title product with following physical-chemical constants:

TLC CH$_2$Cl$_2$:MeOH:NH$_4$OH=90:9:0.5 0.527
IR (KBr) cm$^{-1}$ 3451, 2972, 2938, 2879, 2787, 1744, 1638, 1458, 1414, 1381, 1163, 1113, 1078, 1050, 1002, 949, 896, 835, 781, 670.
FAB-MS, MH$^+$ 617.3
$^1$H NMR (300 MHz, CDCl$_3$) δ 5.59 (H-13), 4.46 (H-1'), 4.26 (H-11), 3.59 (H-5), 3.59 (H-5'), 3.58 (H-9a), 3.55 (H-10), 3.49 (12-O—CH$_3$), 3.27 (H-2'), 2.58 (H-2), 2.53 (H-3'), 2.38 (H-8), 2.36 (H-9b), 2.27/3'N(CH$_3$)$_2$/, 2.09 (H-4), 1.75 (H-14a), 1.69 (H-4'a), 1.59 (H-14b), 1.47 (H-7a), 1.33 (6-CH$_3$), 1.32 (10-CH$_3$), 1.32 (2-CH$_3$), 1.30 (H-4'b), 1.25 (5'-CH$_3$), 1.22 (H-7b), 1.16 (12-CH$_3$), 1.03 (8-CH$_3$), 1.01 (4-CH$_3$), 0.93 (14-CH$_3$).
$^{13}$C NMR (75 MHz, CDCl$_3$) δ 174.5 (C-1), 156.6 (9a,11 C=O), 106.1 (C-1'), 93.6 (C-5), 79.3 (C-11), 77.6 (C-3), 73.0 (C-13), 75.3 (C-12), 73.8 (C-6), 70.1 (C-2'), 69.9 (C-5'), 65.2 (C-3'), 58.1 (C-10), 53.2 (12-O—CH$_3$), 49.6 (C-9), 44.4 (C-2), 40.0/3'N(CH$_3$)$_2$/, 36.9 (C-7), 36.9 (C-4), 27.9 (C-4'), 25.2 (6-CH$_3$), 25.6 (C-8), 20.9 (5'-CH$_3$), 20.5 (8-CH$_3$), 20.6 (C-14), 15.8 (2-CH$_3$), 16.1 (12-CH$_3$), 13.6 (10-CH$_3$), 10.1 (14-CH$_3$), 7.6 (4-CH$_3$).

Method B:

By hydrolysis of 4",12-di-O-methyl-9-deoxo-9-dihydro-9a-aza-9a-homoerythromycin A 9a,11-cyclic carbamate (0.45 g) in a mixture of 96% ethanol (25 ml) and 0.25 N HCl (10 ml), by the same procedure as described in Method A, on pH 9.5 title compound (0.26 g) was isolated.

Example 4

2'-O-Acetyl-3-decladinosyl-3-oxy-12-O-methyl-9-deoxo-9-dihydro-9a-aza-9a-homoerythromycin A 9a,11-cyclic carbamate To a solution of 3-decladinosyl-3-oxy-12-O-methyl-9-deoxo-9-dihydro-9a-aza-9a-homoerythromycin A 9a,11-cyclic carbamate (0.6 g, 0.972 mmola) from Example 3. in CH$_2$Cl$_2$ (25 ml) NaHCO$_3$ (0.22 g, 2.62 mmola) and acetic acid anhydride (0.125 ml, 1.33 mmola) were added and it was then stirred for 4 hours at room temperature. Isolation was the same one as in Example 2. yielding the title product (0.55 g) with following physical-chemical constants:

TLC CH$_2$Cl$_2$:MeOH:NH$_4$OH=90:9:0.5 0.582
IR (KBr) cm$^{-1}$ 3442, 2973, 2938, 2879, 2786, 1744, 1460, 1417, 1381, 1250, 1166, 1113, 1050, 1004, 949.
FAB-MS, MH$^+$ 659.4

Example 5

3-Decladinosyl-3-oxy-12-O-ethyl-9-deoxo-9-dihydro-9a-aza-9a-homoerythromycin A 9a,11-cyclic carbamate Method A:

To a solution of 12-O-ethyl-9-deoxo-9-dihydro-9a-aza-9a-homoerythromycin A 9a,11-cyclic carbamate (1.00 g, 1.27 mmol) in 96% ethanol (50 ml) 2N hydrochloric acid (20 ml) was added and the reaction mixture was stirred for 48 hours at room temperature. Ethanol was evaporated, CHCl$_3$ (50 ml) was added and the pH of the mixture was about pH 1.0. Layers were separated and the water layer extracted two more times with CHCl$_3$. PH value of water layer was adjusted on pH 9.5 and then extracted three times with CHCl$_3$. Combined organic extracts at pH 9.5 were rinsed with brine, dried over K$_2$CO$_3$ and evaporated yielding crude product which was purified by chromatography on a silica gel column using the system CH$_2$Cl$_2$:MeOH:NH$_4$OH=90:9:0.5. The combining and evaporating of chromatographically homogenous fractions gave the title product (0.71 g) with following physical-chemical constants:

TLC CH$_2$Cl$_2$:MeOH:NH$_4$OH=90:9:0.5 0.29
IR (KBr) cm$^{-1}$ 3449, 2973, 2936, 2785, 1745, 1638, 1459, 1414, 1381, 1320, 1251, 1218, 1163, 1113, 1051, 1003, 948, 895, 836, 7687, 689.
ESI-MS, MH$^+$ 631.8
$^1$H NMR (500 MHz, CDCl$_3$) δ 5.59 (H-13), 4.47 (H-1'), 4.25 (H-11), 3.94 (12-O—CH$_2$a/Et), 3.77 (H-3), 3.58 (H-5'), 3.57 (H-5), 3.56 (12-O—CH$_2$b/Et), 3.52 (H-9a), 3.50 (H-10), 3.05 (H-2'), 2.57 (H-2), 2.51 (H-3'), 2.47 (H-8), 2.36 (H-9b), 2.24/3'N(CH$_3$)$_2$/, 2.08 (H-4), 1.68 (H-14a), 1.67 (H-4'a), 1.55 (H-14b), 1.29 (10-CH$_3$), 1.25 (6-CH$_3$), 1.21 (4'-Hb), 1.19 (2-CH$_3$), 1.17 (5'-CH$_3$), 1.14 (7-Ha), 1.09 (12-CH$_3$), 1.09 (12-O-Me/Et), 1.00 (4-CH$_3$), 1.00 (8-CH$_3$), 0.90 (14-CH$_3$).
$^{13}$C NMR (75 MHz, CDCl$_3$) δ 174.6 (C-1), 156.9 (9a,11-C=O), 106.7 (C-1'), 94.3 (C-5), 79.7 (C-11), 78.1 (C-3), 76.1 (C-12), 75.7 (C-13), 73.6 (C-6), 70.5 (C-2'), 70.4 (C-5'), 65.8 (C-3'), 60.8 (12-O—CH$_2$/Et), 58.6 (C-10), 50.1 (C-9), 44.8 (C-2), 40.5/3'N(CH$_3$)$_2$/, 37.4 (C-7), 37.1 (C-4), 28.3 (C-4'), 26.1 (C-8), 25.8 (6-CH$_3$), 21.1 (8-CH$_3$), 21.1 (14-C), 20.9 (5'-CH$_3$), 17.2 (2-CH$_3$), 16.3 (12-O-Me/Et), 15.8 (12-CH$_3$), 14.1 (10-CH$_3$), 10.6 (14-CH$_3$), 8.0 (4-CH$_3$).

Method B:

By hydrolysis of 4",12-di-O-ethyl-9-deoxo-9-dihydro-9a-aza-9a-homoerythromycin A 9a,11-cyclic carbamate (1.00 g) in a mixture of 96% ethanol (50 ml) and 2 N HCl (20 ml), by the same procedure as described in Method A, on pH 9.5 title compound (0.76 g) was isolated.

Example 6

2'-O-Acetil-3-decladinosyl-3-oxy-12-O-etil-9-deoxo-9-dihydro-9a-aza-9a-homoerythromycin A 9a,11-cyclic carbamate To a solution of 3-decladinosyl-3-oxy-12-O-ethyl-9-deoxo-9-dihydro-9a-aza-9a-homoerythromycin A 9a,11-cyclic carbamate (1.00 g, 1.59 mmola) from Example 5. in CH$_2$Cl$_2$ (50 ml) NaHCO$_3$ (0.67 g, 7.98 mmola) and acetic acid anhydride (0.18 ml, 1.90 mmola) were added and it was then stirred for 4 hours at room temperature. Isolation was the same one as in Example 2. yielding the title product (1.05 g) with following physical-chemical constants:

TLC CH$_2$Cl$_2$:MeOH:NH$_4$OH=90:9:0.5 0.32
IR (KBr) cm$^{-1}$ 3483, 2973, 2878, 2789, 1747, 1578, 1459, 1413, 1380, 1249, 1166, 1113, 1050, 1006, 947, 897, 770.
ESI-MS, MH$^+$ 673.7

Example 7

2'-O-Acetyl-3-decladinosyl-3,6-hemiketal 9-deoxo-9-dihydro-9a-aza-9a-homoerythromycin A 9a,11-cyclic carbamate To a solution of 2'-O-acetyl-3-decladinosyl-3-oxy-9-deoxo-9-dihydro-9a-aza-9a-homoerythromycin A 9a,11-cyclic carbamate (2.83 g, 4.39 mmola) from Example 2. in $CH_2Cl_2$ (50 ml) dimethylsulfoxide (4.08 ml, 5.32 mmola) and N,N-dimethyl-aminopropyl-ethyl-carbodiimid (5.05 g, 26.34 mmola) were added. The reaction mixture was cooled to 15° C., a then, keeping the temperature constant, solution of pyridinium trifluoracetate (5.01 g, 20.21 mmola) in $CH_2Cl_2$ (10 ml) was added dropwise during 30 minutes. The reaction mixture was stirred at 15° C. to room temperature for additional 2 hours. To the reaction mixture saturated aqueous solution of NaCl (25 ml) was added and the pH value was adjusted to pH 9.5. The layers were separated and the water layer was extracted two more times with $CH_2Cl_2$ Combined organic extracts were rinsed with brine, $NaHCO_3$ and water, dried over $K_2CO_3$ and evaporated yielding 2.5 g of the title product with following physical-chemical constants:

TLC $CH_2Cl_2$:MeOH:$NH_4$OH=90:9:0.5 0.709
IR (KBr) cm$^{-1}$ 3488, 2975, 2939, 2879, 2784, 1748, 1655, 1459, 1373, 1243, 1191, 1169, 1114, 1061, 1011, 968, 912, 797, 763.
FAB MS, MH$^+$ 643.3
$^1$H NMR (300 MHz, CDCl$_3$) δ 4.97 (H-13), 4.81 (H-2'), 4.59 (H-10), 4.26 (H-1'), 4.23 (H-11), 3.63 (H-5), 3.51 (H-5'), 3.44 (H-9a), 2.82 (H-9b), 2.71 (H-3'), 2.43 (H-2), 2.27/3'N(CH$_3$)$_2$/, 2.08 (2'-COCH$_3$), 1.95 (H-14a), 1.85 (H-4), 1.85 (H-7a), 1.74 (H-4'a), 1.74 (H-8), 1.55 (H-7b), 1.46 (H-14b), 1.38 (6-CH$_3$), 1.38 (12-CH$_3$), 1.30 (2-CH$_3$), 1.30 (5'-CH$_3$), 1.27 (H-4'b), 1.23 (4-CH$_3$), 1.15 (10-CH$_3$), 1.03 (8-CH$_3$), 0.89 (14-CH$_3$).
$^{13}$C NMR (75 MHz, CDCl$_3$) δ 175.5 (C-1), 169.8 (2'-COCH$_3$), 156.2 (9a,11 C=O), 103.5 (C-3), 103.4 (C-1'), 94.5 (C-5), 84.5 (C-6), 84.4 (C-11), 76.2 (C-13), 73.9 (C-12), 70.5 (C-2'), 69.2 (C-5'), 63.0 (C-3'), 51.9 (C-10), 49.7 (C-2), 49.1 (C-9), 49.2 (C-4), 44.0 (C-7), 39.9/3'N (CH$_3$)$_2$/, 30.3 (C-4'), 30.6 (C-8), 25.2 (6-CH$_3$), 23.6 (8-CH$_3$), 21.6 (C-14), 20.8 (5'-CH$_3$), 17.4 (12-CH$_3$), 14.0 (2-CH$_3$), 13.6 (4-CH$_3$), 12.6 (10-CH$_3$), 10.2 (14-CH$_3$).

Example 8

3-Decladinosyl-3,6-hemiketal 9-deoxo-9-dihydro-9a-aza-9a-homoerythromycin A 9a,11-cyclic carbamate The solution of 2'-O-acetyl-3-decladinosyl-3,6-hemiketal 9-deoxo-9-dihydro-9a-aza-9a-homoerythromycin A 9a,11-cyclic carbamate (2.5 g) from Example 7. in MeOH (50 ml) was stirred for 24 hours at room temperature. The solvent was evaporated and the residue (2.26 g) purified by low-pressure chromatography on a silica gel column using the system $CH_2Cl_2$:MeOH:$NH_4$OH=90:9:1.5. The combining and evaporating of chromatographically homogenous fractions gave the title product (2.06 g) with following physical-chemical constants:

TLC $CH_2Cl_2$:MeOH:$NH_4$OH=90:9:0.5 0.636
IR (KBr) cm$^{-1}$ 3488, 2975, 2939, 2787, 1743, 1655, 1459, 1384, 1259, 1190, 1114, 1079, 1045, 1011, 970, 956, 796.
FAB MS, MH$^+$ 601.2
$^1$H NMR (300 MHz, CDCl$_3$) δ 4.96 (H-13), 4.65 (H-10), 4.24 (H-11), 4.22 (H-1'), 3.72 (H-5), 3.53 (H-5'), 3.45 (H-9a), 3.24 (H-2'), 2.82 (H-9b), 2.49 (H-3'), 2.52 (H-2), 2.29/3'N(CH$_3$)$_2$/, 2.11 (H-4), 1.91 (H-14a), 1.91 (H-7a), 1.75 (H-8), 1.68 (H-4'a), 1.60 (H-7b), 1.50 (H-14b), 1.40 (6-CH$_3$), 1.38 (12-CH$_3$), 1.31 (2-CH$_3$), 1.26 (4-CH$_3$), 1.24 (H-4'b), 1.22 (5'-CH$_3$), 1.14 (10-CH$_3$), 1.04 (8-CH$_3$), 0.89 (14-CH$_3$).
$^{13}$C NMR (75 MHz, CDCl$_3$) δ 175.2 (C-1), 156.0 (9a,11 C=O), 105.8 (C-1'), 103.4 (C-3), 95.0 (C-5), 84.6 (C-11), 84.4 (C-6), 78.0 (C-13), 77.8 (C-3), 73.9 (C-12), 69.5 (C-2'), 69.5 (C-5'), 65.3 (C-3'), 51.8 (C-10), 49.5 (C-2), 49.3 (C-4), 49.2 (C-9), 44.4 (C-7), 40.0/3'N(CH$_3$)$_2$/, 28.0 (C-4'), 30.7 (C-8), 25.4 (6-CH$_3$), 23.7 (8-CH$_3$), 21.6 (C-14), 20.9 (5'-CH$_3$), 17.3 (12-CH$_3$), 13.9 (2-CH$_3$), 13.5 (4-CH$_3$), 12.4 (10-CH$_3$), 10.1 (14-CH$_3$).

Example 9

2'-O-Acetyl-3-decladinosyl-3,6-hemiketal 12-O-methyl-9-deoxo-9-dihydro-9a-aza-9a-homoerythromycin A 9a,11-cyclic carbamate To a solution of 2'-O-acetyl-3-decladinosyl-3-oxy-12-O-methyl-9-deoxo-9-dihydro-9a-aza-9a-homoerythromycin A 9a,11-cyclic carbamate (0.55 g, 0.44 mmola) from Example 4. in $CH_2Cl_2$ (10 ml) dimethylsulfoxide (0.82 ml, 11.54 mmola) and N,N-dimethyl-aminopropyl-ethyl-carbodiimid (1.0 g, 5.22 mmola) were added. The reaction mixture was cooled to 15° C., a then, keeping the temperature constant, solution of pyridinium trifluoracetate (1.0 g, 5.17 mola) in $CH_2Cl_2$ (5 ml) was added dropwise during 30 minutes. The reaction mixture was stirred at 15° C. to room temperature for additional 2 hours and isolated according the procedure described in Example 7. yielding the title compound (0.55 g) with following physical-chemical constants:

TLC $CH_2Cl_2$:MeOH:$NH_4$OH=90:9:0.5 0.867
IR (KBr) cm$^{-1}$ 3442, 2975, 2939, 2879, 2786, 1746, 1459, 1380, 1249, 1191, 1167, 1114, 1051, 1005, 949.
FAB MS, MH$^+$ 657.3

Example 10

3-Decladinosyl-3,6-hemiketal 12-O-methyl-9-deoxo-9-dihydro-9a-aza-9a-homoerythromycin A 9a,11-cyclic carbamate The solution of 2'-O-acetyl-3-decladinosyl-3,6-hemiketal 12-O-methyl-9-deoxo-9-dihydro-9a-aza-9a-homoerythromycin A 9a,11-cyclic carbamate (0.55 g) from Example 9. in MeOH (20 ml) was stirred for 24 hours at room temperature. The solvent was evaporated and the residue (0.45 g) purified by low pressure chromatography on a silica gel column using the system $CH_2Cl_2$:MeOH:$NH_4$OH=90:9:1.5. The combining and evaporating of chromatographically homogenous fractions gave the title product (0.251 g) with following physical-chemical constants:

TLC $CH_2Cl_2$:MeOH:$NH_4$OH=90:9:0.5 0.776
IR (KBr) cm$^{-1}$ 3489, 2974, 2938, 2786, 1759, 1632, 1457, 1427, 1384, 1256, 1189, 1167, 1115, 1071, 1044, 1010, 968.
FAB MS, MH$^+$ 615.3
$^1$H NMR (300 MHz, CDCl$_3$) δ 5.01 (H-13), 4.53 (H-10), 4.35 (H-11), 4.22 (H-1), 3.71 (H-5), 3.53 (H-5'), 3.47 (H-9a), 3.41 (12-O—CH$_3$), 3.24 (H-2'), 2.81 (H-9b), 2.48 (H-3'), 2.51 (H-2), 2.28/3'N(CH$_3$)$_2$/, 2.10 (H-4), 1.91 (H-7a), 1.86 (H-14a), 1.72 (H-8), 1.67 (H-4'a), 1.59 (H-7b), 1.48 (H-14b), 1.40 (6-CH$_3$), 1.35 (12-CH$_3$), 1.31 (2-CH$_3$), 1.26 (4-CH$_3$), 1.22 (5'-CH$_3$), 1.15 (10-CH$_3$), 1.04 (8-CH$_3$), 0.88 (14-CH$_3$).
$^{13}$C NMR (75 MHz, CDCl$_3$)δ 175.7 (C-1), 156.5 (9a,11 C=O), 105.9 (C-1'), 103.3 (C-3), 95.1 (C-5), 83.4 (C-11), 84.4 (C-6), 76.1 (C-13), 77.6 (C-12), 69.6 (C-2'), 69.6 (C-5'), 65.4 (C-3'), 52.4 (C-10), 51.2 (12-O—CH$_3$), 49.6 (C-2), 49.3 (C-4), 49.3 (C-9), 44.7 (C-7), 40.1/3'N(CH$_3$)$_2$/, 28.1 (C-4'), 30.7 (C-8), 25.6 (6-CH$_3$), 24.0 (8-CH$_3$), 21.9 (C-14), 21.0 (5'-CH$_3$), 14.1 (12-CH$_3$), 14.0 (2-CH$_3$), 13.4 (4-CH$_3$), 12.6 (10-CH$_3$), 10.2 (14-CH$_3$).

Example 11

2'-O-Acetyl-3-decladinosyl-3,6-hemiketal 12-O-ethyl-9-deoxo-9-dihydro-9a-aza-9a-homoerythromycin A 9a,11-cyclic carbamate To a solution of 2'-O-acetyl-3-decladinosyl-3-oxy-12-O-ethyl-9-deoxo-9-dihydro-9a-aza-9a-homoerythromycin A 9a,11-cyclic carbamate (0.34 g, 0.51 mmola) from Example 6. in CH$_2$Cl$_2$ (10 ml) dimethylsulfoxide (0.54 ml, 7.60 mmola) and N,N-dimethyl-aminopropyl-ethyl-carbodiimid (0.58 g, 3.03 mmola) were added. The reaction mixture was cooled to 15° C., a then, keeping the temperature constant, solution of pyridinium trifluoracetate (0.59 g, 3.05 mmola) in CH$_2$Cl$_2$ (5 ml) was added dropwise during 30 minutes. The reaction mixture was stirred at 15° C. to room temperature for additional 2 hours and isolated according the procedure described in Example 9. yielding the title compound (0.32 g) with following physical-chemical constants:
TLC CH$_2$Cl$_2$:MeOH:NH$_4$OH=90:9:0.5 0.89
IR (KBr) cm$^{-1}$ 3442, 2975, 2939, 2879, 2786, 1746, 1459, 1380, 1249, 1191, 1167, 1114, 1051, 1005, 949.
ES-MS, MH$^+$ 671.3

Example 12

3-Decladinosyl-3,6-hemiketal 12-O-ethyl-9-deoxo-9-dihydro-9a-aza-9a-homoerythromycin A 9a,11-cyclic carbamate The solution of 2'-O-acetyl-3-decladinosyl-3,6-hemiketal 12-O-methyl-9-deoxo-9-dihydro-9a-aza-9a-homoerythromycin A 9a,11-cyclic carbamate (0.32 g) from Example 11. in MeOH (20 ml) was stirred for 24 hours at room temperature. The solvent was evaporated and the residue (0.30 g) purified by lowpressure chromatography on a silica gel column using the system CH$_2$Cl$_2$:MeOH:NH$_4$OH=90:9:1.5. The combining and evaporating of chromatographically homogenous fractions gave the title product (0.17 g) with following physical-chemical constants:
TLC CH$_2$Cl$_2$:MeOH:NH$_4$OH=90:9:0.5 0.80
IR (KBr) cm$^{-1}$ 3496, 2975, 2936, 2881, 2786, 1759, 1630, 1458, 1427, 1384, 1331, 1255, 1189, 1167, 1116, 1066, 1011, 968, 875, 838, 763, 680.
ES-MS, MH$^+$ 629.4
$^1$H NMR (300 MHz, CDCl$_3$) δ 5.01 (H-13), 4.52 (H-10), 4.35 (H-11), 4.22 (H-1'), 3.75 (12-O—CH$_2$a/Et), 3.71 (H-5), 3.59 (12-O—CH$_2$b/Et), 3.54 (H-5'), 3.46 (H-9a), 3.25 (H-2'), 2.81 (H-9b), 2.52 (H-3'), 2.52 (H-2), 2.31/3'N(CH$_3$)$_2$/, 2.09 (H-4), 1.90 (H-7a), 1.88 (H-14a), 1.732 (H-8), 1.70 (H-4'a), 1.58 (H-7b), 1.48 (H-14b), 1.39 (6-CH$_3$), 1.36 (12-CH$_3$), 1.31 (2-CH$_3$), 1.25 (4-CH$_3$), 1.24 (H-4'b), 1.22 (5'-CH$_3$), 1.15 (10-CH$_3$), 1.14 (12-O—CH$_3$/Et), 1.04 (8-CH$_3$), 0.88 (14-CH$_3$).
$^{13}$C NMR (75 MHz, CDCl$_3$) δ 174.4 (C-1), 155.7 (9a,11 C=O), 105.0 (C-1'), 102.4 (C-3), 94.2 (C-5), 83.5 (C-6), 83.0 (C-11), 76.7 (C-12), 75.6 (C-13), 68.7 (C-2'), 68.7 (C-5'), 64.5 (C-3'), 57.6 (12-O—CH$_2$/Et), 51.7 (C-10), 48.8 (C-2), 48.6 (C-4), 48.5 (C-9), 43.9 (C-7), 39.3/3'N(CH$_3$)$_2$/, 30.07 (C-8), 27.5 (C-4'), 24.8 (6-CH$_3$), 23.1 (8-CH$_3$), 21.2 (C-14), 20.2 (5'-CH$_3$), 15.0 (12-O—CH$_3$/Et), 13.9 (12-CH$_3$), 13.2 (2-CH$_3$), 12.7 (4-CH$_3$), 11.9 (10-CH$_3$), 9.6 (14-CH$_3$).

Example 13

2'-O-Acetyl-3-decladinosyl-3-mesyl 9-deoxo-9-dihydro-9a-aza-9a-homoerythromycin A 9a,11-cyclic carbamate To a solution of 2'-O-acetyl-3-decladinosyl-3-oxy-9-deoxo-9-dihydro-9a-aza-9a-homoerythromycin A 9a,11-cyclic carbamate (1.21 g, 1.88 mmol) from Example 2. in pyridine (60 ml) methylsulphonyl anhydride (1.176 g, 6.75 mmol) was added and the reaction mixture was stirred at room temperature for 4 hours. The solvent was evaporated and the residue was dissolved in CH$_2$Cl$_2$ (50 ml). Saturated aqueous solution of NaHCO$_3$ (50 ml) was added, the layers were separated and the water layer was extracted two more times with CH$_2$Cl$_2$ Combined organic extracts were rinsed with NaHCO$_3$ and brine, dried over K$_2$CO$_3$ and evaporated yielding 1.8 g of crude product with following physical-chemical constants:
TLC CH$_2$Cl$_2$:MeOH:NH$_4$OH=90:9:0.5 0.72
IR (KBr) cm$^{-1}$ 3459, 2973, 2939, 1746, 1651, 1456, 1415, 1374, 1350, 1243, 1174, 1113, 1061, 1001, 913, 769, 701, 670.
FAB-MS, MH$^+$ 723.8

Example 14

3-Decladinosyl-3,6-cyclic ether 9-deoxo-9-dihydro-9a-aza-9a-homoerythromycin A 9a,11-cyclic carbamate To a solution of 2'-O-acetyl-3-decladinosyl-3-mesyl 9-deoxo-9-dihydro-9a-aza-9a-homoerythromycin A 9a,11-cyclic carbamate from Example 13. (1.00 g, 1.38 mmol) in DMF/THF (30 ml/10 ml) suspension (60%) of NaH in mineral oil (0.22 g, 5.53 mmol) was added and the reaction mixture was stirred at 0° C. for 4 hours. The reaction mixture was poured into saturated aqueous solution of NaHCO$_3$ (50 ml), EtOAc (50 ml) was added and the layers were separated. The water layer was extracted two more times with EtOAc. Combined organic extracts were rinsed with NaHCO$_3$ and brine, dried over K$_2$CO$_3$ and evaporated yielding 0.73 g of product. The obtained product was dissolved in MeOH (60 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product (0.65 g) with following physical-chemical constants:
TLC CH$_2$Cl$_2$:MeOH:NH$_4$OH=90:9:0.5 0.59
IR (KBr) cm$^{-1}$ 3450, 2971, 2928, 1740, 1639, 1461, 1383, 1350, 1255, 1170, 1114, 1077, 1044, 999, 974, 945, 912, 864, 767, 635.
FAB-MS, MH$^+$ 585.7
$^1$H-NMR (500 MHz, CDCl$_3$) δ 4.97 (H-13), 4.40 (H-11), 4.29 (10-H), 4.20 (H-1'), 3.73 (H-3), 3.59 (H-5), 3.51 (H-5'), 3.41 (H-9a), 3.21 (H-2'), 2.50 (H-9b), 2.50 (H-3'), 2.48 (H-2), 2.30/3'N(CH$_3$)$_2$/, 2.05 (H-4), 1.85 (H-14a), 1.85 (H-7a), 1.80 (H-8), 1.68 (H-7b), 1.66 (H-4'a), 1.50 (H-14b), 1.34 (12-CH$_3$), 1.27 (H-4'b), 1.25 (4-CH$_3$), 1.23 (5'-CH$_3$), 1.21 (6-CH$_3$), 1.19 (2-CH$_3$), 1.16 (10-CH$_3$), 1.01 (8-CH$_3$), 0.87 (14-CH$_3$).
$^{13}$C-NMR (75 MHz, CDCl$_3$) δ 174.9 (1-C), 156.7 (9a,11-C=O), 104.2 (C-1'), 93.8 (C-5), 85.0 (C-6), 84.3 (C-11), 83.8 (C-3), 77.9 (C-13), 74.7 (C-12), 70.1 (C-5'), 69.8 (C-2'), 65.8 (C-3'), 53.1 (C-10), 50.0 (C-9), 47.7 (C-2), 46.5 (C-4), 44.2 (C-7), 40.6/3'N(CH$_3$)$_2$/, 29.9 (C-8), 28.8 (C-4'), 24.3

(8-CH$_3$), 22.7 (6-CH$_3$), 22.1 (C—), 21.4 (5'-CH$_3$), 19.3 (4-CH$_3$), 17.9 (12-CH$_3$), 15.1 (2-CH$_3$), 13.1 (10-CH$_3$), 10.6 (14-CH$_3$).

Example 15

2'-O-Acetyl-3-decladinosyl-3-mesyl 12-O-methyl-9-deoxo-9-dihydro-9a-aza-9a-homoerythromycin A 9a,11-cyclic carbamate To a solution of 2'-O-acetyl-3-decladinosyl-3-oxy-12-O-methyl-9-deoxo-9-dihydro-9a-aza-9a-homoerythromycin A 9a,11-cyclic carbamate (0.533 g, 0.81 mmol) from Example 4. in pyridine (60 ml) methylsulphonyl anhydride (0.507 g, 2.91 mmol) was added and the reaction mixture was stirred at room temperature for 4 hours and isolated according the procedure described in Example 13. yielding the title compound (0.573 g) with following physical-chemical constants:

TLC CH$_2$Cl$_2$:MeOH:NH$_4$OH=90:9:0.5 0.88
IR (KBr) cm$^{-1}$ 3458, 2974, 2935, 1747, 1637, 1460, 1414, 1374, 1351, 1241, 1173, 1113, 1060, 1000, 915, 765, 707, 670.
FAB-MS, MH$^+$ 737.8

Example 16

3-Decladinosyl-3,6-cyclic ether 12-O-methyl-9-deoxo-9-dihydro-9a-aza-9a-homoerythromycin A 9a,11-cyclic carbamate To a solution of 2'-O-acetyl-3-decladinosyl-3-mesyl 12-O-methyl-9-deoxo-9-dihydro-9a-aza-9a-homoerythromycin A 9a,11-cyclic carbamate from Example 15. (0.487 g, 0.66 mmol) in DMF/THF (12 ml/4 ml) suspension (60%) of NaH in mineral oil (0.107 g, 2.68 mmol) was added and the reaction mixture was stirred at 0° C. for 4 hours. The reaction mixture was poured into saturated aqueos solution of NaHCO$_3$ (50 ml), EtOAc (50 ml) was added and the layers were separated. The water layer was extracted two more times with EtOAc. Combined organic extracts were rinsed with NaHCO$_3$ and brine, dried over K$_2$CO$_3$ and evaporated yielding 0.43 g of product. The obtained product was dissolved in MeOH (60 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product (0.30 g) with following physical-chemical constants:

TLC CH$_2$Cl$_2$:MeOH:NH$_4$OH=90:9:0.5 0.82
IR (KBr) cm$^{-1}$ 3443, 2956, 2926, 1752, 1639, 1462, 1385, 1365, 1255, 1169, 1114, 1076, 1035, 999, 973, 945, 912, 864, 835, 765, 635.
FAB-MS, MH$^+$ 599.9
$^1$H-NMR (500 MHz, CDCl$_3$) δ 5.06 (H-13), 4.63 (H-10), 4.36 (H-11), 4.20 (H-1'), 3.74 (H-3), 3.58 (H-5), 3.51 (H-5'), 3.43 (H-9a), 3.40 (12-O—CH$_3$), 3.21 (H-2'), 2.83 (H-9b), 2.47 (H-3'), 2.47 (H-2), 2.28/3'N(CH$_3$)$_2$/, 2.07 (H-4), 1.86 (H-7a), 1.82 (H-14a), 1.78 (H-8), 1.68 (H-7b), 1.65 (H-4'a), 1.45 (H-14b), 1.33 (12-CH$_3$), 1.27 (H-4'b), 1.25 (4-CH$_3$), 1.24 (5'-CH$_3$), 1.22 (6-CH$_3$), 1.19 (2-CH$_3$), 1.14 (10-CH$_3$), 1.02 (8-CH$_3$), 0.86 (14-CH$_3$).
$^{13}$C-NMR (75 MHz, CDCl$_3$) δ 175.1 (C-1), 157.1 (9a,11-C=O), 104.6 (C-1'), 94.1 (C-5), 84.8 (C-6), 84.5 (C-3), 83.3 (C-11), 78.0 (C-12), 75.9 (C-13), 70.1 (C-5'), 69.9 (C-2'), 65.9 (C-3'), 53.2 (12-O—CH$_3$), 53.1 (C-10), 50.0 (C-9), 47.8 (C-2), 46.5 (C-4), 44.7 (C-7), 40.6/3'N(CH$_3$)$_2$/, 29.9 (C-8), 28.4 (C-4'), 24.4 (8-CH$_3$), 23.0 (6-Me), 22.4 (C-14), 21.5 (5'-CH$_3$), 19.3 (4-CH$_3$), 19.0 (12-CH$_3$), 15.1 (2-CH$_3$), 13.1 (10-CH$_3$), 10.4 (14-CH$_3$).

Example 17

2'-O-Acetyl-3-decladinosyl-3-mesyl 12-O-ethyl-9-deoxo-9-dihydro-9a-aza-9a-homoerythromycin A 9a,11-cyclic carbamate To a solution of 2'-O-acetyl-3-decladinosyl-3-oxy-12-O-ethyl-9-deoxo-9-dihydro-9a-aza-9a-homoerythromycin A 9a,11-cyclic carbamate (0.55 g, 0.82 mmol) from Example 6. in pyridine (30 ml) methylsulphonyl anhydride (0.512 g, 2.94 mmol) was added and the reaction mixture was stirred at room temperature for 4 hours and isolated according the procedure described in Example 13. yielding the title compound (0.607 g) with following physical-chemical constants:

TLC CH$_2$Cl$_2$:MeOH:NH$_4$OH=90:9:0.5 0.90
IR (KBr) cm$^{-1}$ 3444, 2973, 2934, 1747, 1644, 1462, 1416, 1373, 1351, 1244, 1174, 1116, 1060, 1000, 915, 767, 706, 672.
FAB-MS, MH$^+$ 751.3

Example 18

3-Decladinosyl-3,6-cyclic ether 12-O-ethyl-9-deoxo-9-dihydro-9a-aza-9a-homoerythromycin A 9a,11-cyclic carbamate To a solution of 2'-O-acetyl-3-decladinosyl-3-mesyl 12-O-ethyl-9-deoxo-9-dihydro-9a-aza-9a-homoerythromycin A 9a,11-cyclic carbamate from Example 17. (0.450 g, 0.60 mmol) in DMF/THF (12 ml/4 ml) suspension (60%) of NaH in mineral oil (0.097 g, 2.42 mmol) was added and the reaction mixture was stirred at 0° C. for 4 hours. The reaction mixture was poured into saturated aqueos solution of NaHCO$_3$ (50 ml), EtOAc (50 ml) was added and the layers were separated. The water layer was extracted two more times with EtOAc. Combined organic extracts were rinsed with NaHCO$_3$ and brine, dried over K$_2$CO$_3$ and evaporated yielding 0.45 g of product. The obtained product was dissolved in MeOH (60 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product (0.35 g) with following physical-chemical constants:

TLC CH$_2$Cl$_2$:MeOH:NH$_4$OH=90:9:0.5 0.87
IR (KBr) cm$^{-1}$ 3450, 2971, 2928, 1740, 1639, 1461, 1383, 1255, 1170, 1114, 1077, 1044, 999, 974, 945, 912, 864, 835, 767, 635.
FAB-MS, MH$^+$ 613.7
$^1$H-NMR (500 MHz, CDCl$_3$) δ 5.10 (H-13), 4.62 (H-10), 4.32 (H-11), 4.20 (H-1'), 3.75 (12-O—CH$_2$a/Et), 3.72 (H-3), 3.70 (12-O—CH$_2$b/Et), 3.60 (H-5), 3.52 (H-5'), 3.42 (H-9a), 3.27 (H-2'), 2.85 (H-9b), 2.58 (H-3'), 2.46 (H-2), 2.30/3'N(CH$_3$)$_2$/, 2.08 (H-4), 1.85 (H-7a), 1.82 (H-14a), 1.80 (H-8), 1.75 (H-4'a), 1.63 (H-7b), 1.53 (H-14b), 1.35 (12-CH$_3$), 1.32 (H-4'b), 1.28 (5'-CH$_3$), 1.27 (4-CH$_3$), 1.25 (6-CH$_3$), 1.22 (2-CH$_3$), 1.19 (12-O—CH$_3$/Et), 1.15 (10-CH$_3$), 1.05 (8-CH$_3$), 0.88 (14-CH$_3$).
$^{13}$C-NMR (75 MHz, CDCl$_3$) δ 174.7 (C-1), 159.9 (9a,11-C=O), 104.1 (C-1'), 93.9 (C-5), 84,4 (C-11), 83.3 (C-3), 83.1 (C-6), 77.6 (C-12), 75.9 (C-13), 69.7 (C-5'), 69.0 (C-2'), 65.6 (C-3'), 58.4 (12-O—CH$_2$/Et), 52.8 (C-10), 49.7 (C-9), 47.4 (C-2), 46.1 (C-4), 44.3 (C-7), 40.3/3'N(CH$_3$)$_2$/, 30.0 (C-8), 28.7 (C-4'), 24.1 (8-CH$_3$), 22.7 (6-CH$_3$), 22.1 (C-14), 21.5 (5'-CH$_3$), 18.6 (4-CH$_3$), 15.9 (12-O—CH$_3$/Et), 15.1 (12-CH$_3$), 14.5 (2-CH$_3$), 12.9 (10-CH$_3$), 10.4 (14-CH$_3$),

Example 19

3-Decladinosyl-3-O-(4-nitrophenyl)acyl-9-deoxo-9-dihydro-9a-aza-9a-homoerythromycin A 9a,11-cyclic carbamate To a solution of 4-nitrophenylacetic acid (0.644 g, 3.55 mmol) in dry CH$_2$Cl$_2$ (15 ml) TEA (0.504 ml, 3.55 mmol) was added and the reaction mixture was cooled to 0° C. Pyvaloyl chloride (0.469 ml, 3.55 mmol) was added and the reaction mixture was stirred at the same temperature for 30 minutes. To a reaction mixture pyridine (0.966 ml, 11.94 mmol) and the solution of 2'-O-acetyl-3-decladinosyl-3-oxy-9-deoxo-9-dihydro-9a-aza-9a-homoerythromycin A 9a,11-cyclic carbamate from Example 2. (0.70 g, 1.08 mmol) in dry CH$_2$Cl$_2$ (5 ml) were added and the reaction mixture was stirred at 0° C. for 4 hours. Saturated aqueos solution of NaHCO$_3$ (30 ml) was added and the layers were separated. The water layer was extracted two more times with CH$_2$Cl$_2$. Combined organic extracts were rinsed with brine, dried over K$_2$CO$_3$ and evaporated yielding 0.70 g of oily product. The obtained product was dissolved in MeOH (50 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product which was christalised from CH$_2$Cl$_2$:diethylether:n-hexane yielding 0.30 g of the title compound with following physical-chemical constants:

TLC CH$_2$Cl$_2$:MeOH:NH$_4$OH=90:9:0.5 0.67

IR (KBr) cm$^{-1}$ 3459, 2974, 2939, 1747, 1606, 1524, 1456, 1415, 1380, 1347, 1251, 1216, 1164, 1112, 1076, 1045, 1000, 966, 947, 904, 856, 768, 731, 673.

FAB-MS, MH$^+$ 766.3

$^1$H-NMR (600 MHz, CDCl$_3$) δ 8.20 (H-4",H-6"), 7.55 (H-3", H-7"), 5.28 (H-3), 5.13 (H-13), 4.25 (H-11), 4.04 (H-1'), 3.86 (H-1"a), 3.81 (H-1"b), 3.50 (H-5), 3.48 (H-10), 3.46 (H-9a), 3.27 (H-5'), 3.23 (H-2'), 2.76 (H-2), 2.45 (H-4), 2.38 (H-3'), 2.34 (H-9b), 2.34 (H-8), 2.30/3'N(CH$_3$)$_2$/, 1.74 (H-14a), 1.62 (H-4'a), 1.53 (H-14b), 1.37 (H-7a), 1.34 (H-7b), 1.30 (10-CH$_3$), 1.28 (6-CH$_3$), 1.24 (H-4'b), 1.20 (12-CH$_3$), 1.18 (5'-CH$_3$), 1.10 (4-CH$_3$), 0.97 (8-CH$_3$), 0.90 (2-CH$_3$), 0.88 (14-CH$_3$).

$^{13}$C-NMR (125 MHz, CDCl$_3$) δ 172.3 (C-1), 169.7 (1"-C=O), 156.2 (9a,11-C=O), 147.2 (C-5"), 141.1 (C-2"), 130.4 (C-4", C-6"), 123.7 (C-3", C-7"), 103.7 (C-1'), 84.0 (C-5), 80.2 (C-3), 78.2 (C-11), 76.1 (C-13), 74.6 (C-6), 71.7 (C-12), 70.7 (C-2'), 68.6 (C-5'), 66.0 (C-3'), 58.8 (C-10), 49.8 (C-9), 42.7 (C-2), 41.1 (C-1"), 40.3/3'N(CH$_3$)$_2$/, 36.2 (C-7), 36.1 (C-4), 28.3 (C-4'), 26.4 (6-CH$_3$), 25.1 (C-8), 21.0 (5'-CH$_3$), 20.5 (8-CH$_3$), 20.4 (C-14), 15.7 (2-CH$_3$), 15.0 (12-CH$_3$), 14.0 (10-CH$_3$), 10.3 (14-CH$_3$), 8.7 (4-CH$_3$).

Example 20

3-Decladinosyl-3-O-(4-aminophenyl)acyl-9-deoxo-9-dihydro-9a-aza-9a-homoerythromycin A 9a,11-cyclic carbamate To a solution of 3-decladinosyl-3-O-(4-nitrophenyl)acyl-9-deoxo-9-dihydro-9a-aza-9a-homoerythromycin A 9a,11-cyclic carbamate from Example 19. (0.20 g, 0.26 mmol) in conc. acetic acid (25 ml) PtO2xH2O (0.12 g, 0.52 mmol) was added and the reaction mixture was stirred for 2 hours at room temperature under H2 pressure about 30 barrs. The catalyst was filtrated, wasched and the liquor evaporated. To residue was dissolved in CH$_2$Cl$_2$ (30 ml), water (30 ml) was added and the pH value of the mixture was adjusted to pH 9.5. The layers were separated and the organic layer extracted two times with saturated aqueos solution of NaHCO$_3$. Organic layer was dried over K$_2$CO$_3$ and evaporated yielding crude product which was purified by chromatography on a silica gel column using the system CH$_2$Cl$_2$:MeOH:NH$_4$OH=90:3:0.5. The combining and evaporating of chromatographically homogenous fractions gave the title product which was christalised from CH$_2$Cl$_2$:diethylether:n-hexane yielding 0.13 g of the title compound with following physical-chemical constants:

TLC CH$_2$Cl$_2$:MeOH:NH$_4$OH=90:9:0.5 0.57

IR (KBr) cm$^{-1}$ 3445, 2973, 2936, 1747, 1633, 1519, 1456, 1415, 1380, 1252, 11654, 1077, 1044, 1001, 967, 946, 903, 834, 768, 734, 690, 673.

FAB-MS, MH$^+$ 736.3

$^1$H-NMR (500 MHz, CDCl$_3$) δ 7.14 (H-4", H-6"), 6.65 (H-3", H-7"), 5.22 (H-3), 5.14 (H-13), 4.26 (H-11), 4.01 (H-1'), 3.58 (H-5), 3.58 (H-1"a), 3.50 (H-1"b), 3.50 (H-10), 3.43 (H-9a), 3.24 (H-2'), 3.14 (H-5'), 2.77 (H-2), 2.56 (H-3'), 2.47 (H-4), 2.39/3'N(CH$_3$)$_2$/, 2.37 (H-9b), 2.32 (H-8), 1.91 (H-14a), 1.64 (H-4'a), 1.49 (H-14b), 1.33 (H-7a i b), 1.29 (10-CH$_3$), 1.27 (6-CH$_3$), 1.23 (H-4'b), 1.20 (12-CH$_3$), 1.16 (5'-CH$_3$), 1.10 (4-CH$_3$), 0.97 (8-CH$_3$), 0.91 (2-CH$_3$), 0.84 (14-CH$_3$).

Example 21

3-Decladinosyl-3-O-(4-fluorophenyl)acyl-9-deoxo-9-dihydro-9a-aza-9a-homoerythromycin A 9a,11-cyclic carbamate To a solution of 4-fluorophenylacetic acid (0.360 g, 2.35 mmol) in dry CH$_2$Cl$_2$ (15 ml) TEA (0.360 g, 2.35 mmol) was added and the reaction mixture was cooled to 0° C. Pyvaloyl chloride (0.390 g, 2.35 mmol) was added and the reaction mixture was stirred at the same temperature for 30 minutes. To a reaction mixture pyridine (0.696 ml, 7.91 mmol) and the solution of 2'-O-acetyl-3-decladinosyl-3-oxy-9-deoxo-9-dihydro-9a-aza-9a-homoerythromycin A 9a,11-cyclic carbamate from Example 2. (0.50 g, 0.71 mmol) to dry CH$_2$Cl$_2$ (5 ml) were added and the reaction mixture was stirred at 0° C. for 4 hours and for aditionaly 20 hours at room temperature. The reaction mixture was isolated according the procedure described in Example 19. yielding 0.45 g+of oily product. The obtained product was dissolved in MeOH (50 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product which was christalised from CH$_2$Cl$_2$:diethylether:n-hexane yielding 0.24 g of the title compound with following physical-chemical constants:

TLC CH$_2$Cl$_2$:MeOH:NH$_4$OH=90:9:0.5 0.53

IR (KBr) cm$^{-1}$ 3445, 2973, 2938, 1747, 1609, 1511, 1457, 1416, 1380, 1251, 1223, 1164, 1077, 1045, 1001, 967, 945, 905, 834, 768, 690, 673.

FAB-MS, MH$^+$ 739.3

$^1$H-NMR (500 MHz, CDCl$_3$) δ 7.35 (H-4", H-6"), 7.03 (H-3", H-7"), 5.27 (H-3), 5.14 (H-13), 4.27 (H-11), 4.03 (H-1'), 3.72 (H-1"a), 3.66 (H-1"b), 3.52 (H-5), 3.50 (H-10), 3.45 (H-9a), 3.23 (H-2'), 3.21 (H-5'), 2.76 (H-2), 2.50 (H-4), 2.40 (H-3'), 2.34 (H-9b), 2.33 (H-8), 2.32/3'N(CH$_3$)$_2$/, 1.90 (H-14a), 1.62 (H-4'a), 1.50 (H-14b), 1.37 (H-7a i b), 1.29 (10-CH$_3$), 1.29 (6-CH$_3$), 1.24 (H-4'b), 1.22 (12-CH$_3$), 1.18 (5'-CH$_3$), 1.11 (4-CH$_3$), 0.98 (8-CH$_3$), 0.89 (2-CH$_3$), 0.85 (14-CH$_3$).

$^{13}$C-NMR (75 MHz, CDCl$_3$) δ 172.3 (C-1), 169.9 (1"-C=O), 156.5 (9a,11-C=O), 149.5 (C-5"), 140.2 (C-2"), 130.7 (C-4", C-6"), 128.1 (C-3", C-7"), 103.6 (C-1'), 84.9 (C-5), 80.0 (C-3), 78.6 (C-11), 76.3 (C-13), 75.9 (C-6), 71.7 (C-12), 70.3 (C-2'), 69.7 (C-5'), 66.2 (C-3'), 58.7 (C-10), 49.7 (C-9), 43.0 (C-2), 41.8 (C-1"), 40.3/3'N(CH$_3$)$_2$/, 36.3 (C-4), 36.0 (C-7), 28.8 (C-4'), 26.5 (6-CH$_3$), 24.9 (C-8), 20.9 (5'-CH$_3$), 20.8 (C-14), 20.8 (8-CH$_3$), 15.6 (2-CH$_3$), 15.8 (12-CH$_3$), 13.9 (10-CH$_3$), 10.1 (14-CH$_3$), 8.8 (4-CH$_3$).

Example 22

3-Decladinosyl-3-O-(4-methoxyphenyl)acyl-9-deoxo-9-dihydro-9a-aza-9a-homoerythromycin A 9a,11-cyclic carbamate To a solution of 4-methoxphenylacetic acid (0.390 g, 2.35 mmol) in dry CH$_2$Cl$_2$ (15 ml) TEA (0.360 g, 2.35 mmol) was added and the reaction mixture was cooled to 0° C. Pyvaloyl chloride (0.390 g, 2.35 mmol) was added and the reaction mixture was stirred at the same temperature for 30 minutes. To a reaction mixture pyridine (0.696 ml, 7.91 mmol) and the solution of 2'-O-acetyl-3-decladinosyl-3-oxy-9-deoxo-9-dihydro-9a-aza-9a-homoerythromycin A 9a,11-cyclic carbamate from Example 2. (0.50 g, 0.71 mmol) in dry CH$_2$Cl$_2$ (5 ml) were added and the reaction mixture was stirred at 0° C. for 4 hours and for aditionaly 44 hours at room temperature. The reaction mixture was isolated according the procedure described in Example 19. yielding 0.45 g of oily product. The obtained product was dissolved in MeOH (50 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product which was christalised from CH$_2$Cl$_2$:diethylether:n-hexane yielding 0.37 g of the title compound with following physical-chemical constants:

TLC CH$_2$Cl$_2$:MeOH:NH$_4$OH=90:9:0.5 0.57

IR (KBr) cm$^{-1}$ 3459, 2973, 2938, 1747, 1614, 1514, 1456, 1416, 1380, 1300, 1250, 1216, 1164, 1077, 1040, 969, 904, 821, 769, 674.

FAB-MS, MH$^+$ 751.4

$^1$H-NMR (500 MHz, CDCl$_3$) δ 7.27 (H-4", H-6"), 6.87 (H-3", H-7"), 5.24 (H-3), 5.14 (H-13), 4.26 (H-11), 4.04 (H-1'), 3.80 (5"-OMe), 3.66 (H-1"a), 3.60 (H-1"b), 3.50 (H-5), 3.44 (H-10), 3.43 (H-9a), 3.21 (H-2'), 3.18 (H-5'), 2.76 (H-2), 2.48 (H-4), 2.41 (H-3'), 2.35 (H-9b), 2.32 (H-8), 2.30/3'N(CH$_3$)$_2$/, 1.90 (H-14a), 1.60 (H-4'a), 1.49 (H-14b), 1.33 (H-7a i b), 1.29 (10-CH$_3$), 1.24 (6-CH$_3$), 1.24 (H-4'b), 1.21 (12-CH$_3$), 1.17 (5'-CH$_3$), 1.10 (4-CH$_3$), 0.96 (8-CH$_3$), 0.89 (2-CH$_3$), 0.84 (14-CH$_3$).

$^{13}$C-NMR (75 MHz, CDCl$_3$) δ 172.6 (C-1), 171.3 (1"-C=O), 158.85 (C-5"), 156.8 (9a,11-C=O), 130.3 (C-4", C-6"), 125.6 (C-2"), 113.9 (C-3", C-7"), 103.0 (C-1'), 84.9 (C-5), 79.2 (C-3), 78.2 (C-11), 76.3 (C-13), 74.5 (C-6), 71.7 (C-12), 70.5 (C-2'), 69.4 (C-5'), 65.8 (C-3'), 58.8 (C-10), 55.2 (5"-OMe), 49.8 (C-9), 42.7 (C-2), 40.9 (C-1"), 40.3/3'N(CH$_3$)$_2$/, 36.1 (C-4), 36.0 (C-7), 28.4 (C-4'), 26.5 (6-CH$_3$), 25.1 (C-8), 21.1 (5'-CH$_3$), 20.6 (C-14), 20.4 (8-CH$_3$), 15.6 (2-CH$_3$), 15.0 (12-CH$_3$), 14.0 (10-CH$_3$), 10.3 (14-CH$_3$), 8.7 (4-CH$_3$).

Example 23

3-Decladinosyl-3-O-(benzyl)acyl-9-deoxo-9-dihydro-9a-aza-9a-homoerythromycin A 9a,11-cyclic carbamate To a solution of phenylpropionic acid (0.231 g, 1.55 mmol) in dry CH$_2$Cl$_2$ (10 ml) TEA (0.216 ml, 1.55 mmol) was added and the reaction mixture was cooled to 0° C. Pyvaloyl chloride (0.201 ml, 1.55 mmol) was added and the reaction mixture was stirred at the same temperature for 30 minutes. To a reaction mixture pyridine (0.414 ml, 3.41 mmol) and the solution of 2'-O-acetyl-3-decladinosyl-3-oxy-9-deoxo-9-dihydro-9a-aza-9a-homoerythromycin A 9a,11-cyclic carbamate from Example 2. (0.20 g, 0.31 mmol) in dry CH$_2$Cl$_2$ (5 ml) and 4-(dimethylamino)pyridine (0.038 ml, 0.31 mmol) were added and the reaction mixture was stirred at reflux temperature for 10 hours. The reaction mixture was isolated according the procedure described in Example 19. yielding 0.35 g of oily product. The obtained product was dissolved in MeOH (50 ml) was stirred for 24 hours at room temperature. The solvent was evaporated and the crude product was purified by chromatography on a silica gel column using the system CH$_2$Cl$_2$:MeOH:NH$_4$OH=90:3:0.5. The combining and evaporating of chromatographically homogenous fractions gave the title product which was christalised from CH$_2$Cl$_2$:diethylether:n-hexane yielding 0.10 g of the title compound with following physical-chemical constants:

TLC CH$_2$Cl$_2$:MeOH:NH$_4$OH=90:9:0.5 0.78

IR (KBr) cm$^{-1}$ 3444, 2927, 2927, 1743, 1640, 1456, 1417, 1380, 1260, 1215, 1165, 1107, 1079, 1047, 1002, 965, 938, 810, 769, 702, 675.

FAB-S, MH$^+$ 735.6

$^1$H-NMR (500 MHz, CDCl$_3$) δ 7.19-7.13 (H—Ar), 5.24 (H-3), 5.14 (H-13), 4.24 (H-11), 4.02 (H-1'), 3.50 (H-10), 3.45 (H-5), 3.39 (H-9a), 3.23 (H-2'), 3.23 (H-5'), 2.99 (H-2"a i b), 2.77 (H-1"a i b), 2.76 (H-2), 2.53 (H-3'), 2.50 (H-4), 2.45/3'N(CH$_3$)$_2$/, 2.30 (H-9b), 2.30 (H-8), 1.93 (H-14a), 1.66 (H-4'a), 1.50 (H-14b), 1.34 (H-7a i b), 1.29 (10-CH$_3$), 1.28 (H-4'b), 1.25 (6-CH$_3$), 1.21 (12-CH$_3$), 1.21 (5'-CH$_3$), 1.06 (4-CH$_3$), 0.97 (8CH$_3$), 0.96 (2-CH$_3$), 0.86 (14-CH$_3$).

$^{13}$C-NMR (125 MHz, CDCl$_3$) δ 172.6 (C-1), 172.3 (1"-C=O), 156.1 (9a,11-C=O), 140.2 (C-3"), 128.5 (C-4", C-8"), 128.2 (C-5", C-7"), 126.3 (C-6"), 102.8 (C-1'), 84.4 (C-5), 78.9 (C-3), 78.1 (C-11), 75.9 (C-13), 74.4 (C-6), 71.6 (C-12), 70.1 (C-5'), 69.0 (C-2'), 66.0 (C-3'), 58.7 (C-10), 49.7 (C-9), 42.6 (C-2), 40.3/3'N(CH$_3$)$_2$/, 36.1 (C-1"), 36.1 (C-7), 35.9 (C-4), 30.6 (C-2"), 29.1 (C-4'), 26.4 (6-CH$_3$), 25.0 (C-8), 20.9 (5'-CH$_3$), 20.5 (8-CH$_3$), 20.3 (C-14), 15.8 (2-CH$_3$), 14.9 (12-CH$_3$), 13.9 (10-CH$_3$), 10.3 (14-CH$_3$), 8.7 (4-CH$_3$).

Example 24

3-Decladinosyl-3-O-(pyridyltio)acyl-9-deoxo-9-dihydro-9a-aza-9a-homoerythromycin A 9a,11-cyclic carbamate To a solution of 4-pyridyltioacetic acid (0.59 g, 1.55 mmol) in dry CH$_2$Cl$_2$ (20 ml) TEA (0.216 ml, 1.55 mmol) was added and the reaction mixture was cooled to 0° C. Pyvaloyl chloride (0.201 ml, 1.55 mmol) was added and the reaction mixture was stirred at the same temperature for 30 minutes. To a reaction mixture pyridine (0.828 ml, 6.82 mmol) and the solution of 2'-O-acetyl-3-decladinosyl-3-oxy-9-deoxo-9-dihydro-9a-aza-9a-homoerythromycin A 9a,11-cyclic carbamate from Example 2. (0.20 g, 0.31 mmol) in dry CH$_2$Cl$_2$ (5 ml) and 4-(dimethylamino)pyridine (0.038 ml, 0.31 mmol) were added and the reaction mixture was stirred at reflux temperature for 10 hours. The reaction mixture was isolated according the procedure described in Example 19. yielding 0.37 g of oily product. The obtained product was dissolved in MeOH (50 ml) was stirred for 24 hours at room temperature. The solvent was evaporated and the crude product was purified by chromatography on a silica gel column using the system $CH_2Cl_2$:MeOH:$NH_4OH$=90:3:0.5. The combining and evaporating of chromatographically homogenous fractions gave the title product which was christalised from $CH_2Cl_2$:diethylether:n-hexane yielding 0.09 g of the title compound with following physical-chemical constants:

TLC $CH_2Cl_2$:MeOH:$NH_4OH$=90:9:0.5 0.24

IR (KBr) cm$^{-1}$ 3434, 2972, 2934, 1743, 1649, 1574, 1460, 1411, 1375, 1240, 1167, 1062, 999, 946, 806, 769, 708.

FAB-MS, MH$^+$ 754.6

$^1$H-NMR (300 MHz, CDCl$_3$) δ 8.47 (H-4", H-6"), 7.29 (H-3", H-7"), 5.30 (H-3), 5.15 (H-13), 4.24 (H-11), 4.12 (H-1'), 3.98 (H-1"a), 3.95 (H-1"b), 3.50 (H-10), 3.49 (H-5), 3.44 (H-9a), 3.44 (H-2'), 3.34 (H-5'), 2.96 (H-2), 2.52 (H-3'), 2.50 (H-4), 2.33 (H-9b), 2.33 (H-8), 2.32/3'N(CH$_3$)$_2$/, 1.93 (H-14a), 1.78 (H-4'a), 1.53 (H-14b), 1.37 (H-7a), 1.337 (H-7b), 1.31 (10-CH$_3$), 1.30 (6-CH$_3$), 1.24 (H-4'b), 1.23 (5'-CH$_3$), 1.22 (12-CH$_3$), 1.11 (4-CH$_3$), 1.09 (8-CH$_3$), 0.98 (2-CH$_3$), 0.85 (14-CH$_3$).

$^{13}$C-NMR (75 MHz, CDCl$_3$) δ 172.5 (C-1), 168.8 (1"-C=O), 156.4 (9a,11-C=O), 149.5 (C-4", C-6"), 147.3 (C-2"), 120.9 (C-3", C-7"), 103.6 (C-1'), 87.0 (C-5), 81.1 (C-3), 78.4 (C-11), 76.3 (C-13), 74.6 (C-6), 71.7 (C-12), 70.1 (C-2'), 69.1 (C-5'), 66.4 (C-3'), 59.0 (C-10), 49.9 (C-9), 42.8 (C-2), 40.3/3'N(CH$_3$)$_2$/, 36.3 (C-4), 36.1 (C-7), 33.7 (C-1"), 29.5 (C-4'), 26.4 (6-CH$_3$), 25.1 (C-8), 21.0 (5'-CH$_3$), 20.6 (8-CH$_3$), 20.4 (C-14), 15.8 (2-C$_{13}$), 15.2 (12-CH$_3$), 14.1 (10-CH$_3$), 10.4 (14-CH$_3$), 8.8 (4-CH$_3$).

Example 25

3-Decladinosyl-3-O-acetyl-9-deoxo-9-dihydro-9a-aza-9a-homoerythromycin A 9a,11-cyclic carbamate To a solution of 2'-O-acetyl-3-decladinosyl-3-oxy-9-deoxo-9-dihydro-9a-aza-9a-homoerythromycin A 9a,11-cyclic carbamate from Example 2. (0.215 g, 0.321 mmol) in pyridine (6.0 ml, 79.0 mmol) acetic acid anhydride (3.0 ml, 31.6 mmol) was added and the reaxtion mixture was stirred at 60° C. for 10 hours. The reaction mixture was poured into ice water (50 ml), $CH_2Cl_2$ (50 ml) was added and the layers were separated. The water layer was extracted two more times with $CH_2Cl_2$. Combined organic extracts were rinsed with saturated aqueous solution of NaHCO$_3$, brine, dried over K$_2$CO$_3$ and evaporated. The obtained product was dissolved in MeOH (50 ml) was stirred for 24 hours at room temperature. The solvent was evaporated and the crude product was purified by christalisation from $CH_2Cl_2$:diethylether:n-hexane yielding 0.12 g of the title compound with following physical-chemical constants:

TLC $CH_2Cl_2$:MeOH:$NH_4OH$=90:9:0.5 0.50

IR (KBr) cm$^{-1}$ 3478, 2973, 2933, 1739, 1464, 1416, 1380, 1316, 1244, 1169, 1114, 1077, 1041, 1003, 968, 946, 904, 832, 774, 674.

FAB-MS, MH$^+$ 645.6

$^1$H-NMR (500 MHz, CDCl$_3$) δ 5.24 (H-3), 5.16 (H-13), 4.34 (H-11), 4.09 (H-1'), 3.84 (H-1"a), 3.80 (H-1"b), 3.52 (H-10), 3.50 (H-5), 3.48 (H-9a), 3.40 (H-5'), 3.26 (H-2'), 2.81 (H-2), 2.61 (H-3'), 2.51 (H-4), 2.39/3'N(CH$_3$)$_2$/, 2.32 (H-9b), 2.30 (H-8), 2.15 (1"-CH$_3$), 1.93 (H-14a), 1.75 (H-4'a), 1.52 (H-14b), 1.32 (H-7a i b), 1.31 (10-CH$_3$), 1.27 (6-CH$_3$), 1.27 (H-4'b), 1.22 (5'-CH$_3$), 1.21 (12-CH$_3$), 1.12 (4-CH$_3$), 1.09 (8-CH$_3$), 0.96 (2-CH$_3$), 0.87 (14-CH$_3$).

$^{13}$C-NMR (125 MHz, CDCl$_3$) δ 172.6 (C-1), 170.4 (1"-C=O), 156.1 (9a,11-C=O), 102.5 (C-1'), 84.5 (C-5), 78.7 (C-3), 78.1 (C-11), 75.9 (C-13), 74.4 (C-6), 71.6 (C-12), 70.3 (C-2'), 69.3 (C-5'), 65.9 (C-3'), 58.6 (C-10), 49.7 (C-9), 42.6 (C-2), 40.3/3'N(CH$_3$)$_2$/, 35.9 (C-4), 35.8 (C-7), 28.9 (C-4'), 26.4 (6-CH$_3$), 25.1 (C-8), 21.3 (5'-CH$_3$), 20.9 (8-CH$_3$), 20.5 (1"-CH$_3$), 20.3 (C-14), 15.8 (2-CH$_3$), 14.9 (12-CH$_3$), 13.9 (10-CH$_3$), 10.3 (14-CH$_3$), 8.6 (4-CH$_3$).

Example 26

3-Decladinosyl-3-O-(4-nitrophenyl)acyl-12-O-methyl-9-deoxo-9-dihydro-9a-aza-9a-homoerythromycin A 9a,11-cyclic carbamate To a solution of 4-nitrophenylacetic acid (1.100 g, 6.11 mmol) in dry $CH_2Cl_2$ (25 ml) TEA (0.867 ml, 6.11 mmol) was added and the reaction mixture was cooled to 0° C. Pyvaloyl chloride (0.807 ml, 6.11 mmol) was added and the reaction mixture was stirred at the same temperature for 30 minutes. To a reaction mixture pyridine (1.655 ml, 20.45 mmol) and the solution of 2'-O-acetyl-3-decladinosyl-3-oxy-12-O-methyl-9-deoxo-9-dihydro-9a-aza-9a-homoerythromycin A 9a,11-cyclic carbamate from Example 4. (1.220 g, 1.85 mmol) in dry $CH_2Cl_2$ (10 ml) were added and the reaction mixture was stirred at 0° C. for 4 hours. The reaction mixture was isolated according the procedure described in Example 19. yielding 1.1 g of oily product. The obtained product was dissolved in MeOH (50 ml) was stirred for 24 hours at room temperature. The solvent was evaporated and the crude product was purified by chromatography on a silica gel column using the system $CH_2Cl_2$:MeOH:$NH_4OH$=90:3:0.5. The combining and evaporating of chromatographically homogenous fractions gave the title product which was christalised from $CH_2Cl_2$:diethylether:n-hexane yielding 0.78 g of the title compound with following physical-chemical constants:

TLC $CH_2Cl_2$:MeOH:$NH_4OH$=90:9:0.5 0.71

IR (KBr) cm$^{-1}$ 3460, 2974, 1747, 1606, 1523, 1457, 1414, 1347, 1251, 1163, 1077, 1049, 1002, 949, 855, 782, 731, 674.

FAB-MS, MH$^+$ 780.3

$^1$H-NMR (500 MHz, CDCl$_3$) δ 8.21 (H-4",H-6"), 7.55 (H-3", H-7"), 5.59 (H-13), 5.30 (H-3), 4.25 (H-11), 4.04 (H-1'), 3.86 (H-1"a), 3.81 (H-1"b), 3.50 (H-5), 3.48 (H-10), 3.48 (12-O—CH$_3$), 3.46 (H-9a), 3.27 (H-5'), 3.23 (H-2'), 2.76 (H-2), 2.45 (H-4), 2.38 (H-3'), 2.34 (H-9b), 2.34 (H-8), 2.30/3'N(CH$_3$)$_2$/, 1.74 (H-14a), 1.62 (H-4'a), 1.53 (H-14b), 1.37 (H-7a i b), 1.30 (10-CH$_3$), 1.28 (6-CH$_3$), 1.24 (H-4'b), 1.20 (12-CH$_3$), 1.18 (5'-CH$_3$), 1.10 (4-CH$_3$), 0.97 (8-CH$_3$), 0.90 (2-CH$_3$), 0.88 (14-CH$_3$).

$^{13}$C-NMR (125 MHz, CDCl$_3$) δ 172.0 (C-1), 169.8 (1"-C=O), 156.5 (9a,11-C=O), 147.3 (C-5"), 141.2 (C-2"), 130.6 (C-4", C-6"), 123.7 (C-3", C-7"), 103.8 (C-1'), 85.6 (C-5), 80.0 (C-3), 79.4 (C-11), 76.5 (C-13), 74.6 (C-6), 73.6 (C-12), 70.4 (C-2'), 69.4 (C-5'), 66.2 (C-3'), 58.7 (C-10), 53.4 (12-O—CH$_3$), 49.9 (C-9), 42.8 (C-2), 41.4 (C-1"), 40.4/3'N(CH$_3$)$_2$/, 36.3 (C-4), 36.1 (C-7), 28.7 (C-4'), 26.5 (6-CH$_3$), 24.9 (C-8), 21.0 (5'-CH$_3$), 20.8 (8-CH$_3$), 20.8 (C-14), 16.3 (2-CH$_3$), 15.8 (12-CH$_3$), 13.8 (10-CH$_3$), 10.3 (14-CH$_3$), 8.9 (4-CH$_3$).

Example 27

3-Decladinosyl-3-O-(4-aminophenyl)acyl-12-O-methyl-9-deoxo-9-dihydro-9a-aza-9a-homoerythromycin A 9a,11-cyclic carbamate To a solution of 3-decladinosyl-3-O-(4-nitrophenyl)acyl-12-O-methyl-9-deoxo-9-dihydro-9a-aza-9a-homoerythromycin A 9a,11-cyclic carbamate from Example 26. (0.120 g, 0.15 mmol) in conc. acetic acid (25 ml) PtO2xH2O (0.07 g, 0.31 mmol) was added and the reaction mixture was stirred for 2 hours at room temperature under H2 pressure about 20 barrs. The reaction mixture was isolated according the procedure described in Example 20. Chrystaltsation from $CH_2Cl_2$:diethylether:n-hexane yielding 0.068 g of the title compound with following physical-chemical constants:

TLC $CH_2Cl_2$:MeOH:$NH_4OH$=90:9:0.5 0.52

IR (KBr) cm$^{-1}$ 3439, 2973, 2931, 1744, 1631, 1518, 1463, 1416, 1382, 1252, 1165, 1079, 1054, 1001, 944, 901, 799, 690, 674.

FAB-MS, MH$^+$ 750.7

$^1$H-NMR (500 MHz, CDCl$_3$) δ 7.18 (H-4", H-6"), 6.72 (H-3", H-7"), 5.57 (H-13), 5.22 (H-3), 4.24 (H-11), 4.02 (H-1'), 3.58 (H-1"a), 3.56 (H-5), 3.48 (H-10), 3.48 (12-O—CH$_3$), 3.44 (H-1"b), 3.44 (H-9a), 3.24 (H-2'), 3.14 (H-5'), 2.73 (H-2), 2.58 (H-3'), 2.45 (H-4), 2.42 (H-9b), 2.40/3'N(CH$_3$)$_2$/, 2.34 (H-8), 1.75 (H-14a), 1.64 (H-4'a), 1.52 (H-14b), 1.33 (H-7a i b), 1.30 (10-CH$_3$), 1.27 (6-CH$_3$), 1.24 (H-4'b), 1.22 (12-CH$_3$), 1.17 (5'-CH$_3$), 1.13 (4-CH$_3$), 1.05 (8-CH$_3$), 0.96 (2-CH$_3$), 0.92 (14-CH$_3$).

Example 28

3-Decladinosyl-3-O-(4-nitrophenyl)acyl-12-O-ethyl-9-deoxo-9-dihydro-9a-aza-9a-homoerythromycin A 9a,11-cyclic carbamate To a solution of 4-nitrophenylacetic acid (0.440 g, 2.45 mmol) in dry $CH_2Cl_2$ (20 ml) TEA (0.342 ml, 2.45 mmol) was added and the reaction mixture was cooled to 0° C. Pyvaloyl chloride (0.327 ml, 2.45 mmol) was added and the reaction mixture was stirred at the same temperature for 30 minutes. To a reaction mixture pyridine (0.660 ml, 8.24 mmol) and the solution of 2'-O-acetyl-3-decladinosyl-3-oxy-12-O-ethyl-9-deoxo-9-dihydro-9a-aza-9a-homoerythromycin A 9a,11-cyclic carbamate from Example 6. (0.550 g, 0.817 mmol) in dry $CH_2Cl_2$ (10 ml) were added and the reaction mixture was stirred at 0° C. for 4 hours. The reaction mixture was isolated according the procedure described in Example 19. yielding 0.7 g of oily product. The obtained product was dissolved in MeOH (50 ml) was stirred for 24 hours at room temperature. The solvent was evaporated and the crude product was purified by chromatography on a silica gel column using the system $CH_2Cl_2$:MeOH:$NH_4OH$=90:3:0.5. The combining and evaporating of chromatographically homogenous fractions gave the title product which was christalised from $CH_2Cl_2$:diethylether:n-hexane yielding 0.28 g of the title compound with following physical-chemical constants:

TLC $CH_2Cl_2$:MeOH:$NH_4OH$=90:9:0.5 0.77

IR (KBr) cm$^{-1}$ 3459, 2974, 2936, 1747, 1606, 1523, 1456, 1414, 1380, 1347, 1250, 1218, 1163, 1111, 1077, 1048, 1002, 949, 855, 767, 731, 687.

FAB-MS, MH$^+$ 794.6

$^1$H-NMR (500 MHz, CDCl$_3$) δ 8.18 (H-4", H-6"), 7.55 (H-3", H-7"), 5.56 (H-13), 5.26 (H-3), 4.21 (H-11), 4.05 (H-1'), 3.94 (12-O—CH$_2$a i b/Et), 3.84 (H-1"a), 3.80 (H-1"b), 3.54 (H-5), 3.47 (H-10), 3.42 (H-9a), 3.27 (H-5'), 3.23 (H-2'), 2.73 (H-2), 2.54 (H-3'), 2.45 (H-4), 2.38 (H-8), 2.38/3'N(CH$_3$)$_2$/, 2.30 (H-9b), 1.70 (H-14a), 1.66 (H-4'a), 1.54 (H-14b), 1.31 (H-7a i b), 1.29 (10-CH$_3$), 1.24 (6-CH$_3$), 1.24 (H-4'b), 1.16 (12-CH$_3$), 1.13 (5'-CH$_3$), 1.13 (4-CH$_3$), 1.07 (12-O—CH$_3$/Et), 0.95 (8-CH$_3$), 0.87 (2-CH$_3$), 0.84 (14-CH$_3$).

$^{13}$C-NMR (125 MHz, CDCl$_3$) δ 172.0 (C-1), 169.8 (1"-C=O), 156.6 (9a,11-C=O), 147.3 (C-5"), 141.2 (C-2"), 130.5 (C-4", C-6"), 123.8 (C-3", C-7"), 103.6 (C-1'), 85.8 (C-5), 80.0 (C-3), 79.43 (C-11), 75.3 (C-13), 74.6 (C-6), 73.8 (C-12), 70.3 (C-2'), 69.3 (C-5'), 67.7 (C-3'), 60.5 (12-O—CH$_2$/Et), 58.2 (C-10), 49.8 (C-9), 42.8 (C-2), 41.4 (C-1"), 40.3/3'N(CH$_3$)$_2$/, 36.2 (C-7), 36.0 (C-4), 28.8 (C-4'), 26.9 (6-CH$_3$), 24.8 (C-8), 21.1 (C-14), 21.0 (5'-CH$_3$), 20.7 (8-CH$_3$), 16.7 (12-O—CH$_3$/Et), 16.0 (2-CH$_3$), 15.8 (12-CH$_3$), 13.9 (10-CH$_3$), 10.3 (14-CH$_3$), 8.8 (4-CH$_3$).

Example 29

3-Decladinosyl-3-O-(4-aminophenyl)acyl-12-O-ethyl-9-deoxo-9-dihydro-9a-aza-9a-homoerythromycin A 9a,11-cyclic carbamate To a solution of 3-decladinosyl-3-O-(4-nitrophenyl)acyl-12-O-ethyl-9-deoxo-9-dihydro-9a-aza-9a-homoerythromycin A 9a,11-cyclic carbamate from Example 28. (0.150 g, 0.19 mmol) in conc. acetic acid (25 ml) PtO2xH2O (0.086 g, 0.38 mmol) was added and the reaction mixture was stirred for 2 hours at room temperature under H2 pressure about 20 barrs. The reaction mixture was isolated according the procedure described in Example 20. Chrystalisation from $CH_2Cl_2$:diethylether:n-hexane yielding 0.084 g of the title compound with following physical-chemical constants:

TLC $CH_2Cl_2$:MeOH:$NH_4OH$=90:9:0.5 0.58

IR (KBr) cm$^{-1}$ 3425, 2973, 2933, 1742, 1638, 1518, 1466, 1417, 1382, 1253, 1219, 1166, 1103, 1080, 1052, 1003, 968, 948, 903, 803, 799, 690, 673.

FAB-MS, MH$^+$ 764.7

$^1$H-NMR (500 MHz, CDCl$_3$) δ 7.19 (H-4", H-6"), 6.74 (H-3", H-7"), 5.58 (H-13), 5.23 (H-3), 4.23 (H-11), 4.03 (H-1'), 3.98 (12-O—CH$_2$a i b/Et), 3.72 (H-1"a), 3.66 (H-1"b), 3.55 (H-5), 3.50 (H-10), 3.42 (H-9a), 3.24 (H-2'), 3.17 (H-5'), 2.753 (H-2), 2.58 (H-3'), 2.47 (H-4), 2.40/3'N(CH$_3$)$_2$/, 2.36 (H-8), 2.33 (H-9b), 1.75 (H-14a), 1.65 (H-4'a), 1.53 (H-14b), 1.34 (H-7a i b), 1.29 (10-CH$_3$), 1.26 (6-CH$_3$), 1.24 (H-4'b), 1.20 (12-CH$_3$), 1.18 (5'-CH$_3$), 1.13 (4-CH$_3$), 1.11 (12-O—CH$_3$/Et), 1.05 (8-CH$_3$), 0.95 (2-CH$_3$), 0.90 (14-CH$_3$).

The invention claimed is:

1. A compound of formula (I),

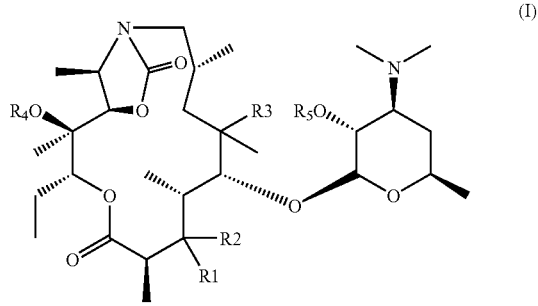

wherein

R$_1$ individually represents hydrogen, hydroxyl or a group of the formula (II),

wherein

X individually represents C$_1$-C$_6$alkyl group, C$_2$-C$_6$alkenyl group; or X individually represents $C_1$-$C_6$alkyl group with at least one incorporated O, S or N atom or X individually represents $(CH_2)_n$—Ar or X individually represents $(CH_2)_n$-heterocycloalkyl, wherein $(CH_2)_n$ individually represents alkyl, wherein n is 1-10, with or without incorporated atom O, S or N, wherein Ar individually represents 5-10-membered monocyclic or bicyclic aromatic ring with 0-3 O, S or N atoms, unsubstituted or substituted with 1-3 groups, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl represents unaromatic, partially or completely saturated 3-10-membered monocyclic or bicyclic ring system, or a 6-membered aromatic or heteroaromatic ring connected with a unaromatic ring with or without incorporated O, S or N atom, unsubstituted or substituted with 1-4 groups which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, —C(O)—, COOH or $R_1$ together with $R_2$ represents ketone, $R_2$ individually represents hydrogen or together with $R_1$ represents ketone or together with $R_3$ forms an ether bond, $R_3$ individually represents hydroxyl, a group of the formula —OX or together with $R_2$ forms an ether bond, $R_4$ individually represents hydrogen, $C_1$-$C_4$alkyl group or $C_2$-$C_4$alkenyl group, and $R_5$ individually represents hydrogen or hydroxyl protected group, or a pharmaceutically acceptable addition salt or hydrate thereof.

2. A Compound according to claim 1, characterised in that $R_1$ represents hydroxyl, $R_2$ and $R_5$ are mutually the same and represents hydrogen, $R_3$ individually represents hydroxyl or for group of the formula —OX, wherein X individually represents $C_1$-$C_6$alkyl group, $C_2$-$C_6$alkenyl group or X individually represents $C_1$-$C_6$alkyl group with at least one incorporated O, S or N atom or X individually represents $(CH_2)_n$—Ar or X individually represents $(CH_2)_n$-heterocycloalkyl, wherein $(CH_2)_n$ individually represents alkyl, wherein n is 1-10, with or without incorporated O, S or N atom, wherein Ar individually represents 5-10-membered monocyclic or bicyclic aromatic ring with 0-3 O, S or N atoms, unsubstituted or substituted with 1-3 groups, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl represents unaromatic, partially or completely saturated 3-10-membered monocyclic or bicyclic ring system, or a 6-membered aromatic or heteroaromatic ring connected with a unaromatic ring with or without incorporated O, S or N atom, unsubstituted or substituted with 1-4 groups, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkil, —C(O)—, COOH and $R_4$ individually stands for hydrogen, $C_1$-$C_4$alkyl group or $C_2$-$C_4$alkenyl group.

3. A Compound according to claim 2, characterised in that $R_4$ represents hydrogen.

4. A Compound according to claim 2, characterised in that $R_4$ represents methyl group.

5. A Compound according to claim 2, characterised in that $R_4$ represents ethyl group.

6. A Compound according to claim 1, characterised in that $R_1$ represents group of the formula (II), wherein X individually represents $C_1$-$C_6$alkyl group, $C_2$-$C_6$alkenyl group or X individually represents $C_1$-$C_6$alkyl group with at least one incorporated O, S or N atom or X individually represents $(CH_2)_n$—Ar or X individually represents $(CH_2)_n$-heterocycloalkyl, wherein $(CH_2)_n$ individually represents alkyl, wherein n is 1-10, with or without incorporated atom O, S or N, wherein Ar individually represents 5-10-membered monocyclic or bycyclic aromatic ring with 0-3 atom O, S or N, unsubstituted or substituted with 1-3 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl represents unaromatic, partially or completely saturated 3-10-membered monocyclic or bicyclic ring system, or a 6-membered aromatic or heteroaromatic ring connected with a unaromatic ring with or without incorporated O, S or N atom, unsubstituted or substituted with 1-4 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, —C(O)—, COOH, $R_2$ and $R_5$ are mutually the same and represent hydrogen, $R_3$ individually represents hydroxyl or group of the formula —OX and $R_4$ individually represents hydrogen, $C_1$-$C_4$alkyl group or $C_2$-$C_4$alkenyl group.

7. A Compound according to claim 1, characterised in that $R_1$ and $R_5$ are mutually the same and represent hydrogen, $R_2$ together with $R_3$ forms an ether bond and $R_4$ individually stands for hydrogen, $C_1$-$C_4$alkyl group or $C_2$-$C_4$alkenyl group.

8. A Compound according to claim 1, characterised in that $R_1$ represents hydroxyl, $R_2$ together with $R_3$ forms an ether bond, $R_5$ represents hydrogen and $R_4$ individually stands for hydrogen, $C_1$-$C_4$alkyl group or $C_2$-$C_4$alkenyl group.

9. A Compound according to claim 1, characterised in that $R_1$ together with $R_2$ stands for keto, $R_3$ represents group of the formula —OX, $R_5$ represents hydrogen and $R_4$ individually represents hydrogen, $C_1$-$C_4$alkyl group or $C_2$-$C_4$alkenyl group.

10. A compound selected from the group consisting of:

3-Decladinosyl-3-oxy-9-deoxo-9-dihydro-9a-aza-9a-homoerythromycin A 9a,11-cyclic carbamate;

3-Decladinosyl-3-oxy-12-O-methyl-9-deoxo-9-dihydro-9a-aza-9a-homoerythromycin A 9a,11-cyclic carbamate;

3-Decladinosyl-3-oxy-12-O-ethyl-9-deoxo-9-dihydro-9a-aza-9a-homoerythromycin A 9a,11-cyclic carbamate; and 2'-O-Acetyl-3-decladinosyl-3-oxy-9-deoxo-9-dihydro-9a-aza-9a-homoerythromycin A 9a,11-cyclic carbamate.

11. A compound selected from the group consisting of:

3-Decladinosyl-3-O-(4-nitrophenyl)acyl-9-deoxo-9-dihydro-9a-aza-9a-homoerythromycin A 9a,11-cyclic carbamate;

3-Decladinosyl-3-O-(4-aminophenyl)acyl-9-deoxo-9-dihydro-9a-aza-9a-homoerythromycin A 9a,11-cyclic carbamate;

3-Decladinosyl-3-O-(4-fluorophenyl)acyl-9-deoxo-9-dihydro-9a-aza-9a-homoerythromycin A 9a,11-cyclic carbamate;

3-Decladinosyl-3-O-(4-methoxyphenyl)acyl-9-deoxo-9-dihydro-9a-aza-9a-homoerythromycin A 9a,11-cyclic carbamate;

3-Decladinosyl-3-O-(benzyl)acyl-9-deoxo-9-dihydro-9a-aza-9a-homoerythromycin A 9a,11-cyclic carbamate;

3-Decladinosyl-3-O-(pyridyltio)acyl-9-deoxo-9-dihydro-9a-aza-9a-homoerythromycin A 9a,11-cyclic carbamate, 3-Decladinosyl-3-O-acetyl-9-deoxo-9-dihydro-9a-aza-9a-homoerythromycin A 9a,11-cyclic carbamate;

3-Decladinosyl-3-O-(4-nitrophenyl)acyl-12-O-methyl-9-deoxo-9-dihydro-9a-aza-9a-homoerythromycin A 9a,11-cyclic carbamate;

3-Decladinosyl-3-O-(4-aminophenyl)acyl-12-O-methyl-9-deoxo-9-dihydro-9a-aza-9a-homoerythromycin A 9a,11-cyclic carbamate;

3-Decladinosyl-3-O-(4-nitrophenyl)acyl-12-O-ethyl-9-deoxo-9-dihydro-9a-aza-9a-homoerythromycin A 9a,11-cyclic carbamate; and 3-Decladinosyl-3-O-(4-aminophenyl)acyl-12-O-ethyl-9-deoxo-9-dihydro-9a-aza-9a-homoerythromycin A 9a,11-cyclic carbamate.

12. A compound selected from the group consisting of:

3-Decladinosyl-3,6-cyclic ether 9-deoxo-9-dihydro-9a-aza-9a-homoerythromycin A 9a,11-cyclic carbamate;

3-Decladinosyl-3,6-cyclic ether 12-O-methyl-9-deoxo-9-dihydro-9a-aza-9a-homoerythromycin A 9a,11-cyclic carbamate; and 3-Decladinosyl-3,6-cyclic ether 12-O-ethyl-9-deoxo-9-dihydro-9a-aza-9a-homoerythromycin A 9a,11-cyclic carbamate.

13. A compound according selected from the group consisting of:

3-Decladinosyl-3,6-hemiketal 9-deoxo-9-dihydro-9a-aza-9a-homoerythromycin A 9a,11-cyclic carbamate;

3-Decladinosyl-3,6-hemiketal 12-O-methyl-9-deoxo-9-dihydro-9a-aza-9a-homoerythromycin A 9a,11-cyclic carbamate; and 3-Decladinosyl-3,6-hemiketal 12-O-ethyl-9-deoxo-9-dihydro-9a-aza-9a-homoerythromycin A 9a,11-cyclic carbamate.

14. A compound according selected from the group consisting of:

2'-O-Acetyl-3-decladinosyl-3-oxy-9-deoxo-9-dihydro-9a-aza-9a-homoerythromycin A 9a,11-cyclic carbamate;

2'-O-Acetyl-3-decladinosyl-3-oxy-12-O-methyl-9-deoxo-9-dihydro-9a-aza-9a-homoerythromycin A 9a,11-cyclic carbamate;

2'-O-Acetyl-3-decladinosyl-3-oxy-12-O-ethyl-9-deoxo-9-dihydro-9a-aza-9a-homoerythromycin A 9a,11-cyclic carbamate;

2'-O-Acetyl-3-decladinosyl-3,6-hemiketal 9-deoxo-9-dihydro-9a-aza-9a-homoerythromycin A 9a,11-cyclic carbamate;

2'-O-Acetyl-3-decladinosyl-3,6-hemiketal 12-O-methyl-9-deoxo-9-dihydro-9a-aza-9a-homoerythromycin A 9a,11-cyclic carbamate; and 2'-O-Acetyl-3-decladinosyl-3,6-hemiketal 12-O-ethyl-9-deoxo-9-dihydro-9a-aza-9a-homoerythromycin A 9a,11-cyclic carbamate.

15. A process for preparation of a compound of formula (I),

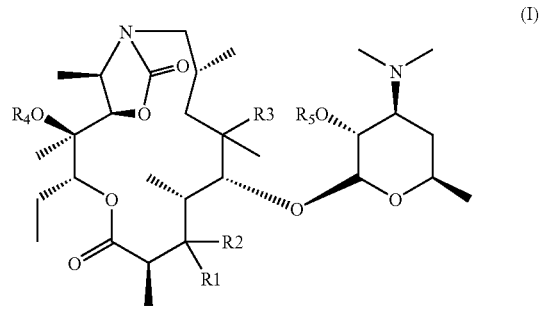

wherein $R_1$ individually represents hydrogen, hydroxyl or a group of the formula (II),

wherein

X individually represents $C_1$-$C_6$alkyl group, $C_2$-$C_6$alkenyl group; or X individually represents $C_1$-$C_6$alkyl group with at least one incorporated O, S or N atom or X individually represents $(CH_2)_n$—Ar or X individually represents $(CH_2)_n$-heterocycloalkyl, wherein $(CH_2)_n$ individually represents alkyl, wherein n is 1-10, with or without incorporated atom O, S or N, wherein Ar individually represents 5-10-membered monocyclic or bicyclic aromatic ring with 0-3 O, S or N atoms, unsubstituted or substituted with 1-3 groups, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl represents unaromatic, partially or completely saturated 3-10-membered monocyclic or bicyclic ring system, or a 6-membered aromatic or heteroaromatic ring connected with a unaromatic ring with or without incorporated O, S or N atom, unsubstituted or substituted with 1-4 groups which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, —C(O)—, COOH or $R_1$ together with $R_2$ represents ketone, $R_2$ individually represents hydrogen or together with $R_1$ represents ketone or together with $R_3$ forms an ether bond, $R_3$ individually represents hydroxyl, a group of the formula —OX or together with $R_2$ forms an ether bond, $R_4$ individually represents hydrogen, $C_1$-$C_4$alkyl group or $C_2$-$C_4$alkenyl group, and $R_5$ individually represents hydrogen or hydroxyl protected group, or a pharmaceutically acceptable addition salt or hydrate thereof, characterised in that a) a compound of formula 3

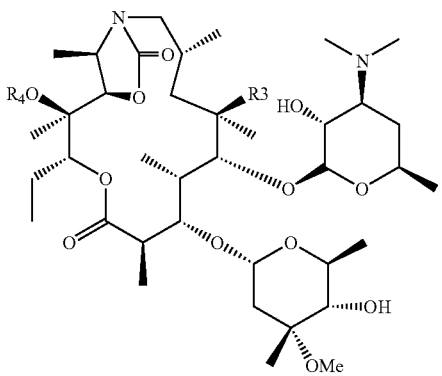

is subjected to hydrolysis with strong acids in a mixture of water and lower alcohols over 10-30 hours at room temperature yielding a compounds of formula (I), wherein $R_1$ represents hydroxyl, $R_2$ and $R_5$ are mutually the same and represents hydrogen, $R_3$ individually represents hydroxyl or a group of the formula —OX, wherein X individually represents $C_1$-$C_6$alkyl group, $C_2$-$C_6$alkenyl group or X individually represents $C_1$-$C_6$alkyl group with at least one incorporated O, S or N atom or X individually represents $(CH_2)_n$—Ar or X individually represents $(CH_2)_n$-heterocycloalkyl, wherein $(CH_2)_n$ individually represents alkyl, wherein n is 1-10, with or without incorporated atom O, S or N, wherein Ar individually represents 5-10-membered monocyclic or bicyclic aromatic ring with 0-3 atom O, S or N, unsubstituted or substituted with 1-3 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkyl, and heterocycloalkyl represents unaromatic, partially or completely saturated 3-10-membered monocyclic or bicyclic ring system, or a 6-membered aromatic or heteroaromatic ring connected with a unaromatic ring with or without incorporated O, S or N atom, unsubstituted or substituted with 1-4 group, which are selected independently from halogen, OH, OMe, $NO_2$, $NH_2$, amino-$C_1$-$C_3$alkyl or amino-$C_1$-$C_3$dialkyl, CN, $SO_2NH_2$, $C_1$-$C_3$alkil, —C(O)—, COOH and $R_4$ individually represents hydrogen, $C_1$-$C_4$alkyl group or $C_2$-$C_4$alkenyl group, which is then subjected to b) a selective acylation of the hydroxyl group at 2'-position with a chlorides or anhydride of a carboxylic acids with up to 4 carbon atoms, in the presence of inorganic or organic base, in a reaction-inert solvent at a temperature from 0-30° C., yielding a 2'-O-acyl derivatives of formula (I), wherein $R_1$ represents hydroxyl, $R_2$ represents hydrogen, $R_3$ individually represents hydroxyl or group of the formula —OX, $R_5$ represents acetyl group and $R_4$ and X have the meanings defined in a)

which is then optionally subjected to c1) a reaction with mixed anhydrides of carboxylic acids of the formula Y—COO—R', wherein Y represents hydrogen or represents group X wherein X is as defined in step a), wherein R' represents a group selected from pivaloyl-, p-toluensulphonyl-, isobutoxycarbonyl-, etoxycarbonyl- and isopropoxycarbonyl-group, in the presence of inorganic or organic base, in a reaction-inert solvent, at a temperature from 0-30° C. for 3-100 hours yielding a compound of formula (I), wherein $R_1$ represents a group of formula (II) as defined above, $R_2$ represents hydrogen, $R_3$ individually represents hydroxyl or the group of the formula —OX, wherein $R_5$ represents acetyl, and substituents $R_4$ and X are as defined in step a), which is then subjected to deprotection with a lower alcohol at a temperature from room temperature to the reflux temperature of the solvent, yielding a compound of formula (I), wherein $R_5$ represents hydrogen and $R_3$, $R_4$ and X have the meanings as defined in c1);

or c2) when $R_3$ represents group of formula OX and the remaining substituents have the meanings defined in b), a compound from step b) is subjected to oxidation of the hydroxyl group in the C-3 position of an aglycone ring with N,N-dimethylaminopropyl-3-ethyl-carbodiimide in the presence of dimethylsulfoxide and pyridinium trifluoracetate as a catalyst in a inert organic solvent at a temperature from 10° C. to room temperature, yielding a compound of general formula (I), wherein $R_1$ together with $R_2$ represents ketone, $R_3$ represents a group of the formula —OX, $R_5$ represents acetyl and substituents $R_4$ and X have the above meanings defined in step a), which is then subjected to deprotection with a lower alcohol at a temperature from room temperature to the reflux temperature of the solvent, yielding a compound of general formula (I), wherein $R_1$ and $R_2$ together represent ketone, wherein $R_5$ represents hydrogen and all other substituents have the meanings as defined in c2);

or c3) when $R_3$ represents hydroxyl and the remaining substituents have the meanings defined in step b), the compound from step b) is subjected to oxidation described in step c) to obtain a 3,6-hemiketal compound of general formula (I) wherein $R_1$ represents hydroxyl, $R_2$ together with $R_3$ forms an ether bond, $R_5$ represents acetyl and $R_4$ has the above meanings, which is then subjected to deprotection with a lower alcohols at a temperature from room temperature to the reflux temperature of the solvent, yielding a compound of formula (I), wherein $R_5$ represents hydrogen and all other substituents have the meanings defined in step c3);

or c4) when $R_3$ represents hydroxyl and the remaining substituents have the meanings defined in step b), hydroxyl group on the C-3 position of a compound from step b) is transformed to a good leaving group, using methylsulfonylchloride, in an inert organic solvent at a temperature from room temperature to the reflux temperature of the solvent for 10-50 hours, then to elimination using sodium hydride, in a inert organic solvent at a temperature from 10° C. to room temperature, yielding a 3,6-cyclic ether compound of formula (I), wherein $R_1$ represents hydrogen, $R_2$ together with $R_3$ represents ether, $R_5$ represents acetyl and $R_4$ has the above meanings, which is then subjected to deprotection with a lower alcohol, at a temperature from room temperature to the reflux temperature of the solvent, yielding a compound of formula (I), wherein $R_5$ stands for hydrogen and all other substituents have the meanings as defined in $C_4$).

* * * * *

UNITED STATES PATENT AND TRADEMARK OFFICE
CERTIFICATE OF CORRECTION

PATENT NO. : 7,358,367 B2
APPLICATION NO. : 10/527940
DATED : April 15, 2008
INVENTOR(S) : Andrea Fajdetic et al.

It is certified that error appears in the above-identified patent and that said Letters Patent is hereby corrected as shown below:

ON THE TITLE PAGE:

Item (54) "PRESENT INVENTION RELATES TO THE NEW 3-DECLADINOSYL DERIVATIVES OF 9-DEOXO-9A-AZA9A-HOMOERYTHROMYCIN A 9A, 11-CYCLIC CARBAMATES" should read -- PRESENT INVENTION RELATES TO THE NEW-3-DECLADINOSYL DERIVATIVES OF 9-DEOXO-9-DIHYDRO-9A-AZA-9A-HOMOERYTHROMYCIN A 9A, 11-CYCLIC CARBAMATES --

COLUMN 28:

Line 65, delete "addition"

COLUMN 29:

Line 49, "chlorides" should read -- chloride -- and "acids" should read -- acid --
Line 52, after "30° C", delete "."
Line 52, "derivatives" should read -- derivative --
Line 66, after "30° C", delete "."

COLUMN 30:

Line 20, after "10° C", delete "."
Line 55, after "10° C", delete "."

Signed and Sealed this

Third Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,358,367 B2
APPLICATION NO. : 10/527940
DATED : April 15, 2008
INVENTOR(S) : Andrea Fajdetic et al.

It is certified that error appears in the above-identified patent and that said Letters Patent is hereby corrected as shown below:

ON THE TITLE PAGE:

Item (54) and Column 1, lines 1-4 "PRESENT INVENTION RELATES TO THE NEW 3-DECLADINOSYL DERIVATIVES OF 9-DEOXO-9A-AZA9A-HOMOERYTHROMYCIN A 9A, 11-CYCLIC CARBAMATES" should read -- PRESENT INVENTION RELATES TO THE NEW-3-DECLADINOSYL DERIVATIVES OF 9-DEOXO-9-DIHYDRO-9A-AZA-9A-HOMOERYTHROMYCIN A 9A, 11-CYCLIC CARBAMATES --

COLUMN 28:

Line 65, delete "addition"

COLUMN 29:

Line 49, "chlorides" should read -- chloride -- and "acids" should read -- acid --
Line 52, after "30° C", delete "."
Line 52, "derivatives" should read -- derivative --
Line 66, after "30° C", delete "."

UNITED STATES PATENT AND TRADEMARK OFFICE
CERTIFICATE OF CORRECTION

PATENT NO. : 7,358,367 B2
APPLICATION NO. : 10/527940
DATED : April 15, 2008
INVENTOR(S) : Andrea Fajdetic et al.

It is certified that error appears in the above-identified patent and that said Letters Patent is hereby corrected as shown below:

COLUMN 30:

Line 20, after "10° C", delete "."
Line 55, after "10° C", delete "."

This certificate supersedes the Certificate of Correction issued March 3, 2009.

Signed and Sealed this

Thirty-first Day of March, 2009

JOHN DOLL
*Acting Director of the United States Patent and Trademark Office*